United States Patent [19]
Bhatnagar et al.

[11] Patent Number: 5,593,840
[45] Date of Patent: Jan. 14, 1997

[54] AMPLIFICATION OF NUCLEIC ACID SEQUENCES

[75] Inventors: Satish K. Bhatnagar; Albert L. George, Jr.; Irina Nazarenko, all of Gaithersburg, Md.

[73] Assignee: Oncor, Inc., Gaithersburg, Md.

[21] Appl. No.: 461,823

[22] Filed: Jun. 5, 1995

Related U.S. Application Data

[63] Continuation-in-part of Ser. No. 168,621, Dec. 16, 1993, which is a continuation-in-part of Ser. No. 10,433, Jan. 27, 1993, abandoned.

[51] Int. Cl.$^6$ .............. C12Q 1/68; C12Q 1/70; C12P 19/34; C07H 21/04
[52] U.S. Cl. ............... 435/6; 435/5; 435/91.1; 435/91.2; 435/91.5; 435/94; 435/183; 536/24.3; 536/24.31; 536/24.33
[58] Field of Search .............. 435/6, 91.1, 91.2, 435/91.5, 5, 183, 94; 536/25.1, 24.3, 24.31, 24.33

[56] References Cited

U.S. PATENT DOCUMENTS 4,683,202  7/1987  Mullis .................... 435/91
5,427,930  6/1995  Birkenmeyer et al. ........ 435/91.52

FOREIGN PATENT DOCUMENTS

WO93/00447  1/1993  WIPO.
WO94/03636  2/1994  WIPO.

Primary Examiner—Bradley L. Sisson
Assistant Examiner—Jeffrey Fredman
Attorney, Agent, or Firm—Glenn E. Karta

[57] ABSTRACT

A process for amplifying nucleic acid sequences from a DNA or RNA template which may be purified, or may exist in a mixture of nucleic acids. The resulting nucleic acid sequences may be exact copies of the template, or may be modified. The process has advantages over prior art amplification processes in that it increases the fidelity of copying a specific nucleic acid sequence, and it allows one to more efficiently detect a particular point mutation in a single assay.

59 Claims, 18 Drawing Sheets

```
1921 GATTGAGAAA GCTGTCAAGG AAGCCAATGC CTATGACTTT ATCATGAAAC TGCCTCATAA
1981 ATTTGACACC CTGGTTGGAG AGAGAGGGGC CCAGTTGAGT GGTGGGCAGA AGCAGAGGAT
2041 CGCCATTGCA CGTGCCCTGG TTCGCAACCC CAAGATCCTC CTGCTGGATG AGGCCACGTC
2101 AGCCTTGGAC ACAGAAAGCG AAGCAGTGGT TCAGGTGGCT CTGGATAAGG CCAGAAAAGG
2161 TCGGACCACC ATTGTGATAG CTCATCGTTT GTCTACAGTT CGTAATGCTG ACGTCATCGC
2221 TGGTTTCGAT GATGGAGTCA TTGTGGAGAA AGGAAATCAT GATGAACTCA TGAAAGAGAA
2281 AGGCATTTAC TTCAAACTTG TCACAATGCA GACAGCAGGA AATGAAGTTG AATTAGAAAA
2341 TGCAGCTGAT GAATCCAAAA GTGAAATTGA TGCCTTGGAA ATGTCTTCAA ATGATTCAAG
2401 ATCCAGTCTA ATAAGAAAAA GATCAACTCG TAGGAGTGTC CGTGGATCAC AAGCCCAAGA
2461 CAGAAAGCTT AGTACCAAAG AGGCTCTGGA TGAAAGTATA CCTCCAGTTT CCTTTTGGAG
2521 GATTATGAAG CTAAATTTAA CTGAATGGCC TTATTTTGTT GTTGGTGTAT TTTGTGCCAT
2581 TATAAATGGA GGCCTGCAAC CAGCATTTGC AATAATATTT TCAAAGATTA TAGGGGTTTT
2641 TACAAGAATT GATGATCCTG AAACAAAACG ACAGAATAGT AACTTGTTTT CACTATTGTT
2701 TCTAGCCCTT GGAATTATTT CTTTTATTAC ATTTTTCCTT CAGGGTTTCA CATTTGGCAA
2761 AGCTGGAGAG ATCCTCACCA AGCGGCTCCG ATACATGGTT TTCCGATCCA TGCTCAGACA
2821 GGATGTGAGT TGGTTTGATG ACCCTAAAAA CACCACTGGA GCATTGACTA CCAGGCTCGC
2881 CAATGATGCT GCTCAAGTTA AAGGGGCTAT AGGTTCCAGG CTTGCTGTAA TTACCCAGAA
2941 TATAGCAAAT CTTGGGACAG GAATAATTAT ATCCTTCATC TATGGTTGGC AACTAACACT
3001 GTTACTCTTA GCAATTGTAC CCATCATTGC AATAGCAGGA GTTGTTGAAA TGAAAATGTT
3061 GTCTGGACAA GCACTGAAAG ATAAGAAAGA ACTAGAAGGT GCTGGGAAGA TCGCTACTGA
3121 AGCAATAGAA AACTTCCGAA CCGTTGTTTC TTTGACTCAG GAGCAGAAGT TTGAACATAT
3181 GTATGCTCAG AGTTTGCAGG TACCATACAG AAACTCTTTG AGGAAAGCAC ACATCTTTGG
3241 AATTACATTT TCCTTCACCC AGGCAATGAT GTATTTTCC TATGCTGGAT GTTTCCGGTT
3301 TGGAGCCTAC TTGGTGGCAC ATAAACTCAT GAGCTTTGAG GATGTTCTGT TAGTATTTTC
3361 AGCTGTTGTC TTTGGTGCCA TGGCCGTGGG GCAAGTCAGT TCATTTGCTC CTGACTATGC
3421 CAAAGCCAAA ATATCAGCAG CCCACATCAT CATGATCATT GAAAAAACCC CTTTGATTGA
3481 CAGCTACAGC ACGGAAGGCC TAATGCCGAA CACATTGGAA GGAAATGTCA CATTTGGTGA
3541 AGTTGTATTC AACTATCCCA CCCGACCGGA CATCCCAGTG CTTCAGGGAC TGAGCCTGGA
3601 GGTGAAGAAG GGCCAGACGC TGGCTCTGGT GGGCAGCAGT GGCTGTGGGA AGAGCACAGT
3661 GGTCCAGCTC CTGGAGCGGT TCTACGACCC CTTGGCAGGG AAAGTGCTGC TTGATGGCAA
3721 AGAAATAAAG CGACTGAATG TTCAGTGGCT CCGAGCACAC CTGGGCATCG TGTCCCAGGA
3781 GCCCATCCTG TTTGACTGCA GCATTGCTGA GAACATTGCC TATGGAGACA ACAGCGGGT
3841 GGTGTCACAG GAAGAGATCG TGAGGGCAGC AAAGGAGGCC AACATACATG CCTTCATCGA
3901 GTCACTGCCT AATAAATATA GCACTAAAGT AGGAGACAAA GGAACTCAGC TCTCTGGTGG
3961 CCAGAAACAA CGCATTGCCA TAGCTCGTGC CCTTGTTAGA CAGCCTCATA TTTTGCTTTT
4021 GGATGAAGCC ACGTCAGCTC TGGATACAGA AAGTGAAAAG GTTGTCCAAG AAGCCCTGGA
4081 CAAAGCCAGA GAAGGCCGCA CCTGCATTGT GATTGCTCAC CGCCTGTCCA CCATCCAGAA
4141 TGCAGACTTA ATAGTGGTGT TTCAGAATGG CAGAGTCAAG GAGCATGGCA CGCATCAGCA
4201 GCTGCTGGCA CAGAAGGCA TCTATTTTC AATGGTCAGT GTCCAGGCTG GAACAAAGCG
4261 CCAGTGAACT CTGACTGTAT GAGATGTTAA ATACTTTTTA ATATTTGTTT AGATATGACA
4321 TTTATTCAAA GTTAAAAGCA AACACTTACA GAATTATGAA GAGGTATCTG TTTAACATTT
4381 CCTCAGTCAA GTTCAGAGTC TTCAGAGACT TCGTAATTAA AGGAACAGAG TGAGAGACAT
4441 CATCAAGTGG AGAGAAATCA TAGTTTAAAC TGCATTATAA ATTTTATAAC AGAATTAAAG
4501 TAGATTTTAA AAGATAAAAT GTGTAATTTT GTTTATATTT TCCCATTTGG ACTGTAACTG
4561 ACTGCCTTGC TAAAAGATTA TAGAAGTAGC AAAAAGTATT GAAATGTTTG CATAAAGTGT
4621 CTATAATAAA ACTAAACTTT CATGTG
```

FIG. 4

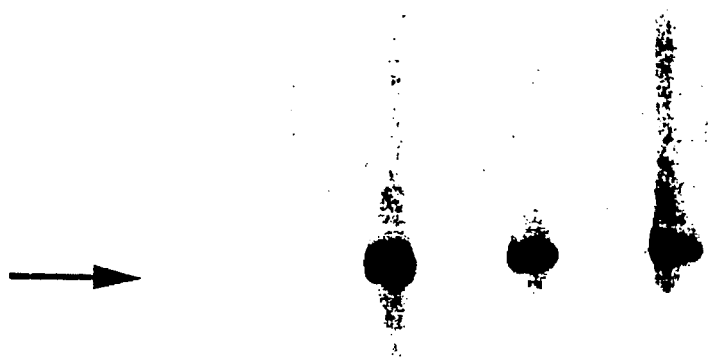
FIG.5
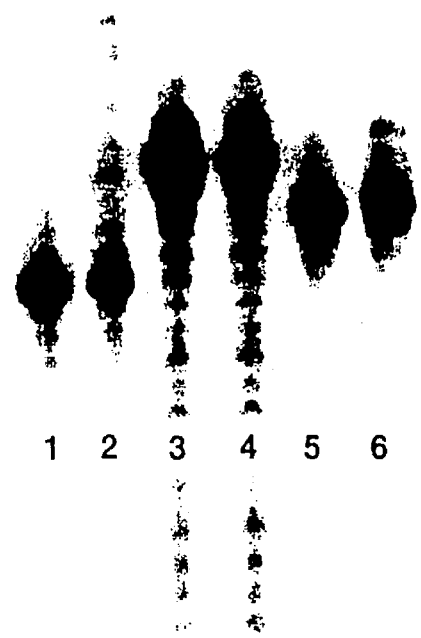
1 2 3 4 5 6

1 2 3 4 5 6

5' AAATGCCCCATAGGTTTTGAACTCACAGATTAAACT    ACCGAGTGTCAGAGGATCTGAGAAGCAGAATT 3'
         (SEQ ID NO:26)                              (SEQ ID NO:27)

3' TACGGGGTATCCAAAACTTGAGTG 5'      3' ACAGTCTCCTAGACTCTTCGT 5'
                   FGA 1 (SEQ ID NO:18)             FGA 2 (SEQ ID NO:17)

FGA 3 (SEQ ID NO:16)
                   5' CCATAGGTTTTGAACTCACAG 3'

3' TTTACGGGGTATCCAAAACTTGAGTGTCTAATTTGA    TGGCTCACAGTCTCCTAGACTCTTCGTCTTAA 5'

Figure 13

SD4(M)G (SEQ ID NO:19)                                Oligo 5 (SEQ ID NO:9)
3' GTCCTTTGTCGATACTGGTACTAATGG 5'            3' CAGCACTGACCCTTTTGGGACCGC 5'
                              *
5' GGAAACAGCTATGACCATGATTACCAATTCGAGCTCCGTCGTCGTGACTGGGAAAACCCTGGCGTT 3'
                         63 mer control template (SEQ ID NO:20)

FIGURE 14

SD4(M)G (SEQ ID NO:19)          SD 23 (SEQ ID NO:24)
3' GTCCTTTGTCGATACTGGTACTAATGGTTAAGCTCGAGGCAGCA 5'
                              *
5' GGAAACAGCTATGACCATGATTACCAATTCGAGCTCCGTCGTCGTGACTGGGAAAACCCTGGCGTT 3'
            63 mer control template (SEQ ID NO:20)

AMPLIFICATION OF NUCLEIC ACID SEQUENCES

CROSS REFERENCE TO RELATED APPLICATION

This application is a continuation-in-part of application Ser. No. 08/168,621 filed Dec. 16, 1993, which is a continuation-in-part of application Ser. No. 08/010,433 filed Jan. 27, 1993, now abandoned.

BACKGROUND OF THE INVENTION

1. Field of the Invention

The present invention relates to a process for amplifying nucleic acid sequences. More specifically, it relates to an improved process for producing nucleic acid sequences from a DNA or RNA template which may be purified, or may exist in a mixture of nucleic acids. The resulting nucleic acid sequences may be exact copies of the template, or may be modified.

2. Description of Related Art

In the past, methods have been employed for amplifying nucleic acid sequences wherein both strands of the nucleic acid sequence to be amplified are synthesized by the same method. Such methods are prone to limitations due to the nature of the enzymes utilized in these processes.

In U.S. Pat. Nos. 4,683,195 and 4,683,202, DNA or RNA is amplified by the polymerase chain reaction (PCR). These patents are incorporated herein by reference in their entirety. This method involves the hybridization of an oligonucleotide primer to the 5' end of each complementary strand of the double-stranded target nucleic acid. The primers are extended from the 3' end in a 5'→3' direction by a DNA polymerase which incorporates free nucleotides into a nucleic acid sequence complementary to each strand of the target nucleic acid. After dissociation of the extension products from the target nucleic acid strands, the extension products become target sequences for the next cycle. In order to obtain satisfactory amounts of the amplified DNA, repeated cycles must be carried out, between which cycles, the complementary DNA strands must be denatured under elevated temperatures.

Traditional polymerases used in this process, such as *E. coli* DNA polymerase I have the limitation of being inactivated at temperatures necessary for the denaturation of the complementary strands. Thus, between each cycle of synthesis by such polymerases and after the heat denaturation step, a fresh aliquot of enzyme must be added to the reaction mixture so that extension of the primer and synthesis of the complementary strand may occur in the following cycle. This additional step increases the time required for amplification and decreases the ease of amplification which requires multiple steps.

In recent years, thermostable DNA polymerases have been discovered and isolated from thermophilic organisms such as *Thermus aquaticus*. Such thermostable polymerases make it possible to add enzyme at the beginning of a series of synthesis and denaturation steps, without the need to add a new aliquot of enzyme after each denaturation step.

A potential problem associated with PCR is the hybridization of a primer sequence to regions of the DNA molecule not intended to be amplified. Generally these undesired hybridizations occur because the target sample contains, in addition to the target sequence itself, other sequences with some complementarity to the primer sequences. If the 3' terminal nucleotides of the primer molecule are successfully hybridized to a sequence other than the target sequence, it is possible that primer extension may be successfully initiated by the polymerase enzyme, leading to the generation of an extension product different from the desired target sequence. Under some circumstances, this extension product will undergo exponential amplification, and be erroneously thought to be the desired target sequence.

A method of detecting a specific nucleic acid sequence present in low copy in a mixture of nucleic acids, called ligase chain reaction (LCR), has also been described. European patent application 0 320 308 describes this method and is incorporated herein by reference in its entirety. Target nucleic acid in a sample is annealed to probes containing contiguous sequences. Upon hybridization, the probes are ligated to form detectable fused probes complementary to the original target nucleic acid. The fused probes are disassociated from the nucleic acid and serve as a template for further hybridizations and fusions of the probes, thus amplifying geometrically the nucleic acid to be detected. The method does not use DNA polymerase.

LCR has disadvantages due to the need for at least four separate oligonucleotide probes for amplification. It also requires that the entire sequence of the target nucleic acid be known. Further, background signal can be caused by target independent ligation of the probes. Since the third probe hybridizes to the first probe and the fourth probe hybridizes to the second probe, the probes, when added in excess, can easily form duplexes among themselves which can be ligated independently of the target nucleic acid.

European Application No. 0 439 182 which is incorporated herein in its entirety by reference discloses a method of improving LCR amplification by providing probes/primers which hybridize to the target nucleic acid wherein one end is modified such that ligation cannot occur until the modified end is corrected. One such modification is the placement of a small gap between the probes preventing ligation of the probes. The gap sequence of the target nucleic acid must be selected such that the DNA sequence is comprised of three or less different nucleotides from the four possible nucleotides. The fourth nucleotide must be the first base complementary to the 5' end of the adjacent probe. The gap is then filled using a DNA polymerase or reverse transcriptase to extend one or more of the probes in a 5' to 3' direction in a target dependent manner to render the probes ligatable. The reaction mixture omits the fourth deoxynucleoside triphosphate complementary to the base at the 5' end of the adjacent probe. Because this method requires that the gap chosen in the target nucleic acid only contains bases which are complementary to a maximum of three of the deoxynucleoside triphosphates, the method limits the location of the gap on the target nucleic acid and also limits the size of the gap. Further, the method requires four primers. The application also discloses a method of PCR amplification wherein one end of the primer is modified such that the primer is not extendable by a polymerase enzyme. When this modification is removed in a template dependent manner, the primer can be extended. However, this type of PCR requires an additional step of removal of the modification before extension can occur.

In view of the foregoing disadvantages attendant with prior art methods of amplifying nucleic acid sequences, it should be apparent that there exists a need in the art for a method in which the fidelity of amplified sequences can be increased, which allows for the detection of a particular nucleic acid strand, and which allows one to efficiently examine multiple alleles in a single series of amplification steps.

SUMMARY OF THE INVENTION

The present invention is based on the discovery that certain aspects of LCR and PCR can be used in combination to detect and amplify a target nucleic acid sequence with increased fidelity. Accordingly, in one of its process aspects, the present invention relates to a process for amplifying enzymatically a target nucleic acid sequence contained in a nucleic acid or a mixture of nucleic acids while substantially avoiding strand displacement by polymerase, comprising the steps of:

a. selecting the target nucleic acid sequence;

b. providing primers, said primers comprising a first primer which is substantially complementary to a first segment at a first end of the target nucleic acid sequence and a second primer which is substantially complementary to a second segment at a second end of the target nucleic acid sequence and whose 3' end is adjacent to the 5' end of the first primer and a third primer which is similar to the first end of the target nucleic acid sequence and which is substantially complementary to at least a portion of said first primer such that when the third primer is hybridized to the first primer, the position of the third primer complementary to the base at the 5' end of the first primer contains a modification which substantially avoids strand displacement under polymerizing conditions;

c. providing at least four different nucleotide bases;

d. hybridizing said first and second primers to the target nucleic acid sequence in a target dependent manner to form a primer-target complex;

e. ligating under conditions such that the adjacent 5' end of the first primer and the 3' end of the second primer will ligate to form a fused amplification product substantially complementary to said target nucleic acid sequence;

f. dissociating said fused amplification product from said target nucleic acid sequence;

g. hybridizing said third primer to said fused amplification product;

h. extending said third primer in the presence of the nucleotide bases under conditions such that an extended amplification product is formed substantially complementary to said fused amplification product and which contains said modification;

i. dissociating the extended amplification product from the fused amplification product;

j. allowing the extended, modified amplification product to hybridize to additional first and second primers in a target dependent manner; and k. ligating the 5' end of the additional first primer to the 3' end of the additional second primer while substantially avoiding strand displacement of the additional first primer, to form additional amplification product.

In another of its process aspects, the present invention relates to a process for detecting enzymatically a point mutation or allele of a target nucleic acid sequence contained in a nucleic acid or a mixture of nucleic acids using the method disclosed above. One of said primers is comprised of a number of similar oligonucleotide sequences, one of which is exactly complementary to the possible allele or point mutation and each of which oligonucleotides is labeled with a different label. The allele is determined by detecting which labeled oligonucleotide is contained within the resulting amplification products.

In a third aspect, the present invention relates to a process for amplifying enzymatically a target nucleic acid sequence contained in a nucleic acid or a mixture of nucleic acids comprising the steps of:

a. selecting the target nucleic acid sequence;

b. providing primers, said primers comprising a first primer which is substantially complementary to a first segment at a first end of the target nucleic acid sequence and a second primer which is substantially complementary to a second segment at a second end of the target nucleic acid sequence said second segment being spaced a number of nucleotides from said first segment and a third primer which is similar to the first end of the target nucleic acid sequence and which is substantially complementary to at least a portion of said first primer, said portion including the 5' end of the first primer such that when the third primer is hybridized to the first primer, the position of the third primer complementary to the base at the 5' end of the first primer contains a modification which substantially avoids strand displacement under polymerizing conditions;

c. providing at least four different nucleotide bases;

d. hybridizing said first and second primers to the target nucleic acid sequence in a target dependent manner to form a primer-target complex;

e. extending the 3' end of the second primer in the presence of the nucleotide bases under conditions such that an extended second primer is formed wherein the 3' end of the extended second primer terminates at a base adjacent to the 5' end of the first primer;

f. ligating the ends of the first primer and extended second primer under conditions such that said first and said second primers will form a fused amplification product substantially complementary to said target nucleic acid sequence;

g. dissociating said fused amplification product from said target nucleic acid sequence;

h. hybridizing said third primer to said fused amplification product;

i. extending said third primer in the presence of the nucleotide bases under conditions such that an extended modified amplification product is formed substantially complementary to said fused amplification product and which contains said modification;

j. allowing the extended, modified amplification product to hybridize to additional first and second primers in a target dependent manner;

k. extending the 3' end of the additional second primer in the presence of the nucleotide bases under conditions such that an extended additional second primer is formed wherein the 3' end of the extended additional second primer terminates at a base adjacent to the 5' end of the additional first primer; and l. ligating the 5' end of the additional first primer to the 3' end of the additional second primer while substantially avoiding strand displacement of the additional first primer, to form additional amplification product.

In one of its product aspects, the present invention relates to a kit for amplifying a target nucleic acid sequence contained in a nucleic acid or a mixture of nucleic acids comprising: first, second, and third primers and optionally a fourth primer as described above; a ligating enzyme; a polymerizing enzyme; and at least four nucleotides.

BRIEF DESCRIPTION OF THE DRAWINGS

FIG. 4 shows a portion of the sequence of the multidrug resistance gene (MDR-1) (SEQ ID NO:1).

FIGS. 5–11 are printouts from a Phosphor Imager of a scanned acrylamide gel which show amplification achieved with various embodiments of the present invention.

FIGS. 13–14 depict other embodiments of the method of DNA amplification/detection as set forth herein.

FIG. 16 depicts an experiment which shows that a template modification according to the present invention does not have a significant effect on DNA ligase activity.

DESCRIPTION OF THE PREFERRED EMBODIMENTS

Figure 1:
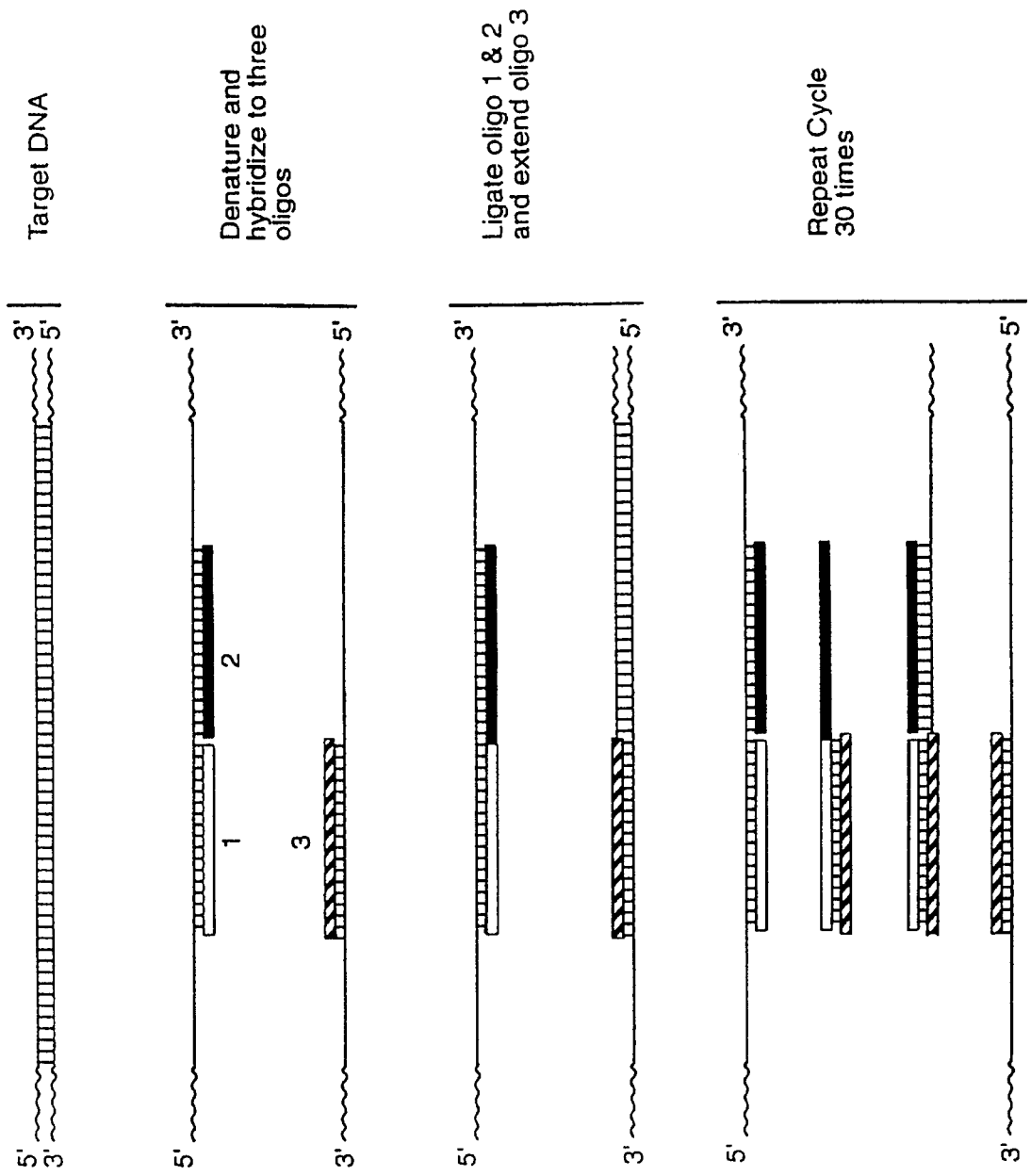
FIG. 1 depicts one embodiment of the method of DNA amplification/detection as set forth herein.

Prior to discussing this invention in detail, the following terms will first be defined:

The "target nucleic acid" or "target nucleic acid sequence" suitable for use in the present invention may be taken from prokaryotic or eukaryotic DNA or RNA, including from plants, animals, insects, microorganisms, etc., and it may be isolated or present in samples which contain nucleic acid sequences in addition to the target nucleic acid sequence to be amplified. The target nucleic acid sequence may be located on a nucleic acid strand which is longer than the target nucleic acid sequence. In this case, the ends of the target nucleic acid sequence are the boundaries with the unselected nucleic acid sequence and the target nucleic acid sequence. The target nucleic acid sample may be obtained synthetically, or can be isolated from any organism by methods well known in the art. Particularly useful sources of nucleic acid are derived from tissues or blood samples of an organism, nucleic acids which are present in self-replicating vectors, and nucleic acids derived from viruses and pathogenic organisms such as bacteria and fungi. Also particularly useful for the present invention are target nucleic acid sequences which are related to disease states, such as those caused by chromosomal rearrangement, insertions, deletions, translocations and other mutations, those caused by oncogenes, and those associated with cancer.

The term "selected" means that a target nucleic acid sequence having the desired characteristics is located and probes are constructed around appropriate segments of the target sequence.

The term "probe" or "primer" has the same meaning herein, namely, an oligonucleotide fragment which is single stranded. The term "oligonucleotide" means DNA or RNA.

A probe or primer is "substantially complementary" to the target nucleic acid sequence if it hybridizes to the sequence under renaturation conditions so as to allow target dependent ligation or extension. Renaturation depends on specific base pairing between A–X (where X is T or U) and G–C bases to form a double stranded duplex structure. Therefore, the primer sequence need not reflect the exact sequence of the target nucleic acid sequence. However, if an exact copy of the target nucleic acid is desired, the primer should reflect the exact sequence. Typically, a "substantially complementary" primer will contain at least 70% or more bases which are complementary to the target nucleic segment. More preferably 80% of the bases are complementary and most preferably 90% of the bases are complementary. Generally, the primer must hybridize to the target nucleic acid sequence at the end to be ligated or extended to allow target dependent ligation or extension.

The primers may be RNA or DNA, and may contain modified nitrogenous bases which are analogs of the normally incorporated bases, or which have been modified by attaching labels or linker arms suitable for attaching labels. Inosine may be used at positions where the target sequence is not known, or where it may be degenerate. The oligonucleotides must be sufficiently long to allow hybridization of the primer to the target nucleic acid and to allow amplification to proceed. They are preferably 15 to 50 nucleotides long, more preferably 20 to 40 nucleotides long, and most preferably 25 to 35 nucleotides long. The nucleotide sequence, content and length will vary depending on the sequence to be amplified.

It is contemplated that a primer may comprise one or more oligonucleotides which comprise substantially complementary sequences to the target nucleic acid sequence. Thus, under less stringent conditions, each of the oligonucleotides would hybridize to the same segment of the target nucleic acid. However, under increasingly stringent hybridization conditions, only that oligonucleotide sequence which is most complementary to the target nucleic acid sequence will hybridize. The stringency of conditions is generally known to those in the art to be dependant on temperature, solvent and other parameters. Perhaps the most easily controlled of these parameters is temperature and since the conditions here are similar to those of PCR, one skilled in the art could determine the appropriate conditions required to achieve the level of stringency desired.

Oligonucleotide primers or oligonucleotide probes suitable for use in the present invention may be derived by any method known in the art, including chemical synthesis, or by cleavage of a larger nucleic acid using non-specific nucleic acid-cleaving chemicals or enzymes, or by using site-specific restriction endonucleases.

The primers may be prepared using the β-cyanoethylphosphoramidite method or other methods known in the art. A preferable method for synthesizing oligonucleotide primers is conducted using an automated DNA synthesizer by methods known in the art. Once the desired oligonucleotide primer is synthesized, it is cleaved from the solid support on which it was synthesized, and treated, by methods known in the art, to remove any protecting groups present. The oligonucleotide primer may then be purified by any method known in the art, including extraction and gel purification. The concentration and purity of the oligonucleotide primer may be examined on an acrylamide gel, or by measuring the optical densities at 260 and 280 nm in a spectrophotometer.

In order for the ligase to ligate the oligonucleotide primers, the primers used in the present invention are preferably phosphorylated at their 5' ends. This may be achieved by any method known in the art, but is preferably conducted with the enzyme T4 polynucleotide kinase. The oligonucleotides can be phosphorylated in the presence of unlabeled or labeled ATP. In order to monitor the amplification process, labeled ATP may be used to phosphorylate the primers. Particularly preferable is [γ-$^{32}$P] ATP.

The oligonucleotide primers may alternatively be labeled with any detectable marker known in the art, including other radioactive nuclides such as $^{35}$S or $^{3}$H and the like, fluorescent markers such as fluorescein, rhodamine, Texas red, Lucifer yellow, AMCA blue and the like, or with enzymatic markers which may produce detectable signals when a particular chemical reaction is conducted, such as alkaline phosphatase or horseradish peroxidase. Such enzymatic markers are preferably heat stable, so as to survive the denaturation steps of the amplification process. Primers may be indirectly labeled by incorporating a nucleotide covalently linked to a hapten or other molecule such as biotin to which a labeled avidin molecule may be bound, or digoxygenin, to which a labeled anti-digoxygenin antibody may be bound.

Primers may be labeled during chemical synthesis or the label may be attached after synthesis by methods known in the art. The method of labeling and the type of label is not critical to this invention.

It is contemplated that the probes or primers may be modified. For example the hydrolysis of a primer by 5' to 3' exonuclease associated with polymerase may be prevented by placing a phosphorothioate group between the last nucleotides of the 5' end of the primer. The extension of a primer by polymerase can be blocked by placing a dideoxynucleotide, an amino group, a cordycepin, or a phosphate group at the 3' end. Alternatively, the extension of a primer may be blocked by placing an arabinosyl nucleotide at the 3' end of the primer which blocks extension by polymerase but allows ligation of the primer to another primer.

The term "the four different nucleotide bases" shall refer to deoxythymidine triphosphate (dTTP); deoxyadenosine triphosphate (dATP); deoxyguanosine triphosphate (dGTP); and deoxycytidine triphosphate (dCTP), when the context is DNA, but shall refer to uridine triphosphate (UTP); adenosine triphosphate (ATP); guanosine triphosphate (GTP); and cytidine triphosphate (CTP) when the context is RNA. Alternatively, dUTP, dITP, dITP, rITP or any other modified base may replace one of the four nucleotide bases or may be included along with the four nucleotide bases in the reaction mixture so as to be incorporated into the amplified strand. The amplification steps are conducted in the presence of at least the four deoxynucleoside triphosphates (dATP, dCTP, dGTP and dTTP) or a modified nucleoside triphosphate to produce a DNA strand, or in the presence of the four ribonucleoside triphosphates (ATP, CTP, GTP and UTP) or a modified nucleoside triphosphate to produce an RNA strand from extension of the oligonucleotide which acts as a primer.

Where the presence of a particular mutation or allele is to be detected by the methods of this invention, one of the oligonucleotide primers may comprise a set of oligonucleotide fragments, each differing in sequence and each labeled by a different method. That oligonucleotide fragment which is exactly complementary to the target DNA sequence will be detected by the presence of that label in the amplification products. In this case, each oligonucleotide fragment may be labeled as described above.

Utility
First Embodiment

In a first embodiment, the target nucleic acid is described as single stranded. However, this should be understood to include the case where the target is actually double stranded but is simply separated from its complementary strand prior to hybridization with probes/primers. Primers one and two, together, are substantially complementary to the target nucleic acid sequence and hybridize to adjacent regions of the target nucleic acid strand such that upon hybridization of the two primers to the target nucleic acid strand the 5' end of the first primer is adjacent to the 3' end of the second primer. The 3' end of the first primer is substantially complementary to the 5' end of the target nucleic acid sequence and the 5' end of the second primer is substantially complementary to the 3' end of the target nucleic acid sequence. The 5' end of the first primer is ligated to the 3' end of the second primer using ligase to create a fused amplification product in a double stranded complex. The fused primer is dissociated from the target nucleic acid.

The third primer is substantially complementary to all or at least a portion of the first primer and is similar to the 5' end of the target nucleic acid. The third primer should be complementary to enough of the first primer so that specific hybridization is achieved under the conditions used. The third primer may be smaller than the first primer or it may be larger than the first primer and also be substantially complementary to a portion of the second primer. The third primer is hybridized to the fused amplification product and extended by polymerase in the presence of at least four different nucleotide bases to form an extended amplification product which is substantially complementary to the fused amplification product. This comprises the first cycle.

Subsequently the double stranded complexes are dissociated. The oligonucleotide primers (1 and 2) are hybridized to the target nucleic acid sequence and the extended amplification product from the first cycle. Primer 3 is hybridized to the fused amplification product. Extension and ligation occur as before and the process can be repeated.

It is contemplated that the 3' end of the second primer may be modified to block the extension of the second primer by polymerase while still allowing ligation of the 3' end of the second primer to the 5' end of the first primer. Such modification may be, for example, the placement of an arabinosyl nucleotide at the 3' end of the second primer. Methods for the chemical synthesis of DNA oligomers containing cytosine arabinoside are known in the art (Beardsley, *Nucl. Acid. Res.* (1988) 16:9165–9176). Such a modification does not need to be removed prior to the ligation of the first and second primers.

Alternatively, it is also contemplated that the 5' end of the first primer can be modified to prevent the hydrolysis of the primer by a 5' to 3' exonuclease associated with a polymerase. Such a modification may be, for example, the placement of a phosphorothioate group between the last nucleotides of the 5' end of the first primer. Methods for the chemical synthesis of phosphorothioate containing primers is known in the art (Ott and Eckstein, *Biochemistry,* (1987) 26:8237–8241). Such a modification does not need to be removed prior to ligation of the first and second primers.

It is further contemplated that extension of the first primer can be prevented without affecting the ligation of this primer by modifying the 3' end of the primer with a dideoxynucleotide or a phosphate group. The method for producing this modification is known in the art (Markiewicz and Wyrzykiewicz, *Nucl. Acid. Res.* (1989) 17:7149–7158).

It has been found that the process can be conducted sequentially without isolation or purification of the products or removal of the excess reagents. Accordingly, this will allow the entire process to be conducted in a single reaction medium (e.g. a test tube).

It is understood that the single strand variation is a more specialized version of the double strand variation. If the target nucleic acid is double stranded some of the third primers will hybridize to the second complementary strand and the first and second primers will hybridize to the first strand. The extension and ligation from the first strand will proceed as described above. Some of the third primers will also be extended in a target specific manner complementary to the second strand. After dissociation of the extended third primer and the second strand, at least some of the first and second primers will hybridize to the extended third primer and at least some of the third primer will again hybridize to the second strand.

Where the target nucleic acid amplified by ligation of the first and second primers and extension of the third primer is to be detected, one or all of these primers may be labeled using a marker as described above to render the amplified target nucleic acid detectable or by conducting the extension of the third primer in the presence of a labeled base, or a base which is activated for labeling.

Alternatively, where the target nucleic acid is double stranded, both amplified strands may be labeled with different detectable markers: the first strand may be labeled by labeling the third primer with a particular marker; and the second strand may be labeled by labeling the first and/or second primer.

In the case where the presence of a particular point mutation or allele is to be detected, one primer comprising a mixture of oligonucleotides is added to the nucleic acid sample. Each oligonucleotide may be labeled with different, separately detectable markers, so that information regarding the presence of a particular mutation or allele may be obtained in a single step. The oligonucleotide which is exactly complementary to the target sequence will be included in the amplification product whereas the other oligonucleotides will not and its presence detected by determining which label is included in the product.

The amplification reaction is optimally conducted with an excess of primers at a ratio of oligonucleotide primers:target of approximately $10^7$ to $10^3$:1, more preferably approximately $10^4$:1. It is contemplated that adjusting the molarity of the primers will maximize the efficiency of the process.

The buffer used for amplification is preferably in a pH range of about 7.5–8.5, more preferably about 8–8.5, and most preferably about 8.0.

Second Embodiment

In a second embodiment, the target nucleic acid is described to be single stranded. However, this should be understood to include the case where the target is actually double stranded, but is simply separated from its complementary strand prior to hybridization with the probes/primers.

The target nucleic acid is hybridized to two primers. The first primer is substantially complementary to the 5' end of the target nucleic acid sequence and the second primer is substantially complementary to the 3' end of the target nucleic acid sequence. The primers (primers one and two) hybridize to regions of the target nucleic acid strand such that upon hybridization of the two primers to the target nucleic acid strand the 5' end of the first primer is spaced from the 3' end of the second primer. The size of the space or gap between the primers is determined by the ability of a polymerase or transcriptase to extend the second primer such that the newly added 3' end of the second primer is directly adjacent to the 5' end of the first primer. Preferably, but not necessarily, the size of the gap or space is sufficiently long such that at least four different nucleotides would be required by the polymerase or transcriptase in order to extend the second primer to "fill in" the gap.

The 3' end of the second primer is extended by polymerase or transcriptase in the presence of the four nucleotide bases. The 5' end of the first primer is then ligated to the new 3' end of the second extended primer to form a double-stranded complex comprising the target nucleic acid and an extended fused primer.

Figure 12:
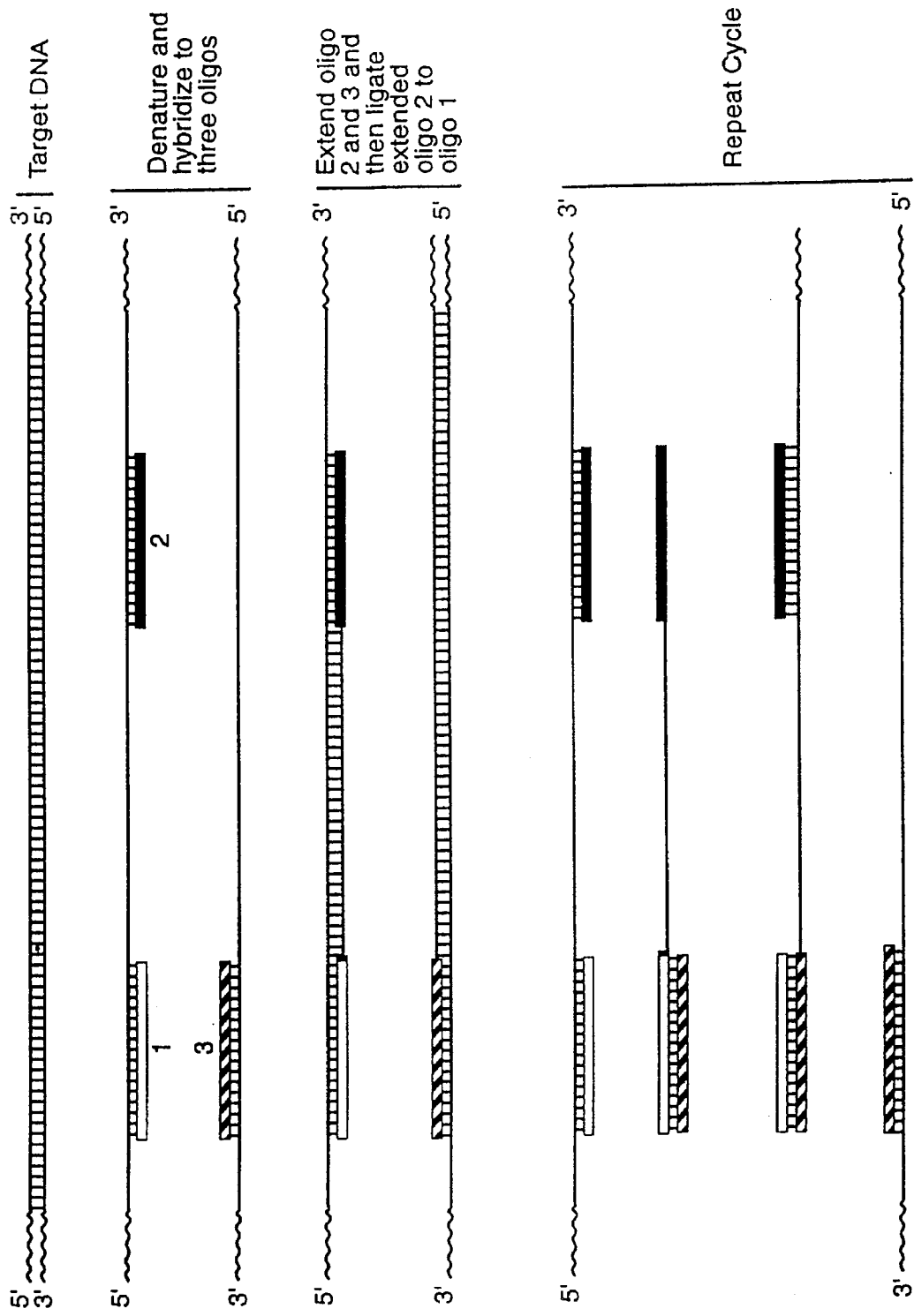
FIG. 12 depicts another embodiment of the method of DNA amplification/detection as set forth herein.

The double stranded complex is dissociated and a third primer is hybridized to the extended fused primer. The third primer is substantially complementary to all or a portion of the first primer and is similar to the 5' end of the target nucleic acid sequence. The 3' end of the third primer is extended by polymerase or transcriptase to form a double-stranded complex and complete the cycle. The double-stranded complex is dissociated and the cycle repeated until the target nucleic acid is amplified. It will be understood that when the target sequence is part of a double stranded nucleic acid as shown in FIG. 12, some of the third primers present will hybridize to the second strand complementary to the target sequence, and will be extended to form an amplification product.

It is contemplated that the process can be conducted sequentially without isolation or purification of the products or removal of the excess reagents. Accordingly, this will allow the entire process to be conducted in a single reaction medium (e.g. a test tube). Further, because the gap between the primers can be any size as discussed above, the method is not limited to a particular DNA sequence and extension of the third primer can proceed in the presence of four nucleotides.

It is understood that the single strand variation is a more specialized case of the double strand variation wherein there are four primers and the first and second primers are substantially complementary to the first strand of the target nucleic acid and the third and fourth primers are substantially complementary to the second strand of the target nucleic acid. The third primer is substantially complementary to at least a portion of the first primer and the fourth primer is substantially complementary to at least a portion of the second primer. The extension and ligation of the third and fourth primers occurs as described above for the first and second primers. It will be understood that at least some of the third and fourth primers will hybridize to the extended fused primer (first and second primers). The third primer is then extended and ligation to the fourth primer occurs.

It is contemplated that the 5' end of the first primer (and the 5' end of the fourth primer, where the nucleic acid is double stranded) can be modified to prevent the hydrolysis of the primer by a 5' to 3' exonuclease associated with the polymerase. Such a modification may be, for example, the placement of a phosphorothioate group between the last nucleotides of the 5' end of the first or fourth primers. Methods for the chemical synthesis of phosphorothioate containing primers is known in the art (Ott and Eckstein, *Biochemistry*, (1987) 26:8237–8241). Such a modification does not need to be removed prior to ligation of the first and second primers.

In connection with the "gap filling" embodiments of the present invention, it will be appreciated that certain DNA polymerases possess a DNA polymerising associated strand displacement activity. It is preferable to reduce or eliminate that activity, as it could lead to displacement of the nonextended primer. For example, referring to FIG. 3, unless this activity is reduced or eliminated, the extension of oligo 2 or oligo 3 could result in the displacement of oligo 1 or oligo 4, respectively. The same problem can be present in the "non gap" embodiments of the present invention. For example, referring to FIG. 1, the polymerase designed to extend oligo 3 could also act to extend oligo 3 while displacing oligo 1 from the target strand.

Strand displacement activity is related to the processivity of the DNA polymerase. Processivity of DNA polymerase is defined as the number of nucleotide residues added per enzyme binding event. A DNA polymerase enzyme with a high degree of processivity will show a strong strand displacement activity. The processivity of the enzyme is affected by factors such as 1) salt concentration, 2) nucleotide concentration, and 3) divalent cations. We have found that:

1) Increasing the salt concentration during primer extension will lower the processivity, there by decreasing the displacement of the companion oligo. This will promote ligation to the extended product.

2) Decreasing the nucleotide concentration of the residue at the 5'-end of the oligo not being extended (oligos 1 and 4 in FIG. 3) will cause the DNA polymerase to pause before incorporating the limiting nucleotide during primer extension. Pausing at the 5'-end of primer 1 extends the time for DNA ligase to seal the gap.

3) Placing a non-extendable arabinosyl derivative of the nucleotide at the 3'-end of the oligo being extended will prevent both the extension of primer 2 and the displacement of primer 1 by DNA polymerase. This helps in the "no gap" version where by primer 1 and primer 2 are positioned adjacently.

It is further contemplated that extension of the first and fourth primers can be prevented without affecting the ligation of these primers by modifying the 3' end of the primers with a dideoxynucleotide or a phosphate group. This method of producing this modification is known in the art (Markiewicz and Wyrzykiewicz, *Nucl. Acid. Res.* (1989) 17:7149–7158).

Another way to decrease or eliminate strand displacement is to modify the template to contain a modification at the proper position which causes polymerase to pause or dissociate at that position. In primer extension by DNA polymerase on a normal DNA template (containing one or more of deoxy adenosine, cytosine, guanosine, and thymidine monophosphate, and phosphodiester internucleotide linkages), the nucleotide incorporation is governed by Watson-Crick base pairing. Modification in the template could have an inhibitory effect on DNA polymerase activity. The possible mechanism for this arrest of DNA synthesis could be the distortion of the primer:template binding site or loss of base coding property at the modification site. Examples of some of the modifications in the template that can affect DNA polymerase are an abasic site, pyrimidine dimers, ribonucleotides, thymine glycol, arabinosylcytosine, etc. See Moore & Strauss, *Nature*, 278, 664–66 (1979); Sagher & Strauss, *Biochemistry*, 22, 4518–26 (1983); Clark & Beardsley, *Biochemistry*, 26, 5398–5403 (1987); Mikita & Beardsley, *Biochemistry*, 27, 4698–4705 (1988).

Arrest of DNA chain elongation by incorporating a synthetic modification in the template can be applied to the present amplification technique for preventing strand displacement. A modification in DNA for the purpose of this technique can be defined as any modification in the DNA that will inhibit bypass by DNA polymerase. Examples of some of the modifications that can be easily incorporated into DNA are arabinosyl derivatives of AMP, CMP, GMP, TMP and LIMP; ribonucleotides; 2'-O-alkylribonucleotides; 2'-O-methylribonucleotides; hypoxanthine; xanthine; inosine; abasic site; synthetic bases such as 1-(2'-deoxy-b-D-ribofuranosyl)-3-nitropyrrole; methyl phosphonate internucleotide linkage, etc. It is preferred that the presence of the modification in the template should not inhibit the DNA ligase activity more than it inhibits the DNA polymerase activity.

An illustration of the present method may be seen by referring to FIG. 13. The target DNA is a partial sequence of the human fibrinogen alpha chain gene (GenBank, Accession No. M64982) from nucleotide 2821 to nucleotide 3104. FGA 1, FGA 2 and FGA 3 are three oligonucleotide primers designed to amplify the TCTT tetranucleotide repeat in that region of the gene. The oligos have the following sequences:

Oligo FGA 3:
5' CCATAGGTTT TGAACTCACA G 3' (SEQ ID NO: 16)
Oligo FGA 2:
5' TGCTTCTCAG ATCCTCTGAC A 3' (SEQ ID NO: 17)
Oligo FGA 1:
5' GTGAGTTCAA AACCTATGGG GCAT- $NH_2$ - 3'
(SEQ ID NO: 18)

During the first cycle of amplification FGA 1 and FGA 2 will hybridize to the upper complementary strand of the target DNA. FGA 2 will be extended by DNA polymerase until it reaches the 5' end of FGA 1, where the nick will be sealed by DNA ligase. FGA 3 will hybridize to the lower complementary target strand and will be extended by DNA polymerase. In the second and subsequent cycles, FGA 2 extended and ligated to FGA 1 will also become a template for FGA 3, and extended product from FGA 3 will also act as template for FGA 1 and FGA 2. According to the present invention, there is a modification in the oligo FGA 3 across from where the 5' end of oligo FGA 1 hybridizes. During the amplification cycle FGA 1 and FGA 2 will hybridize to the extended FGA 3. FGA 2 will be extended by DNA polymerase until it reaches one nucleotide before the modification site on the FGA 3 template and the 5' end of the blocking oligo FGA 1. The presence of this modification in the template will have an inhibitory effect on DNA polymerase, causing it to pause and/or dissociate. This will allow DNA ligase to seal the nick between extended FGA 2 and 5' end of FGA 1, thus preventing strand displacement.

A synthetic modification at a specific position can be introduced in to the oligonucleotide primer during oligo synthesis. The details and methods of such introduction would be well known to one of ordinary skill.

Prevention of strand displacement by this method has several advantages when amplifying long targets or targets having difficult sequence such as nucleotide repeats or G/C rich sequences. Synthesis of these difficult targets require very processive DNA polymerases. Decreasing processivity by increasing salt and/or decreasing dNTP concentration to prevent strand displacement could have an adverse effect on amplification of such targets. Inhibiting strand displacement by having a modification in the oligonucleotide primer as described can overcome these problems, because this allows DNA polymerase to be used under otherwise high processivity conditions.

In another aspect of the present invention, the cycling efficiency and yield of the amplified product may be increased by suitable primer design. In the present amplification technique using three primers (FIG. 12), oligos 1 & 2 hybridize to one strand of the target DNA, whereas oligo 3 hybridizes to the other complementary target strand. Oligo 2 is extended by DNA polymerase and ligated to oligo 1.

Oligo 3 is only extended by DNA polymerase. Exponential amplification occurs because the products formed in one cycle are used as a substrate in subsequent cycles. This means that most of the amplification is achieved on templates generated by extended oligo 3 and ligation of oligo 1 to extended oligo 2 (refer to FIG. 12). As noted previously, the third primer is substantially complementary to all or at least a portion of the first primer. During any amplification cycle, oligo 1 and oligo 3 will not only hybridize to their respective template targets but will also hybridize to each other. It may be suggested that oligo 1 should be used in molar excess over oligo 2 and 3. However, since the kinetics of hybridization are driven also by the concentration of oligos, it is very likely that most of the free oligo 3 will hybridize to free oligo 1 instead of to its template, thereby reducing the efficiency of cycling. It has also been suggested (PCT WO 94/03630) that the length (and/or Tm) of the oligos should be designed such that the order of oligo hybridization to their respective template targets should be oligo 1, then oligo 2 followed by oligo 3. Referring to FIG. 12, it is apparent that the system cannot be designed based on oligo size so that oligo 1 will hybridize first to its target template before hybridizing to oligo 3. The best that can be done is to have their Tm's the same. This would still have the problem of removing the free oligo 3 from the amplification mixture and thus low efficiency. Also since the 5' end of oligo 1 and 3' end of oligo 3 would form a blunt end, the additional problem of blunt end ligation will arise. This not only will give unwanted products, but again reduce the efficiency of amplification.

To overcome that problem, in one aspect of the present invention, the oligonucleotides are designed to increase the probability of oligo 3 hybridizing first to its target sequence and then to oligo 1. The length and/or $T_m$ of the oligos should be such that the preferred order of hybridization will be such that the target will hybridize first with oligo 3 then with oligo 1 followed by oligo 2. This will avoid the problem of oligo 3 hybridizing to oligo 1 before hybridizing to its target and should enhance the efficiency of amplification. This order of hybridization will also assure that the blocker oligo 1 has already hybridized to its proper site before the extended oligo 2 reaches there.

Where the target nucleic acid amplified is to be detected, one or all of these primers may be labeled as described above to render the amplified strand detectable. Alternatively the strand may be labeled by conducting the extension of the second or third primer in the presence of a labeled base, or a base which is activated for labeling.

In the case where one primer comprises a mixture of oligonucleotides to detect the presence of a particular sequence, each of the oligonucleotides may be labeled with different, separately detectable markers, so that information regarding each mutation may be obtained in a single step.

The amplification reaction is optimally conducted with an excess of primers at a ratio of oligonucleotide primers:target of approximately $10^7$ to $10^3$:1, more preferably approximately $10^4$:1. It is contemplated that adjustment of the molarity of the primers will maximize the efficiency of the process.

The buffer used for amplification is preferably in a pH range of about 7–9, more preferably about 8–9, and most preferably about 8.75.

If the target nucleic acid is double stranded, the strands should be separated so that they can be used individually. This separation can be accomplished by any suitable denaturation method including physical, chemical or enzymatic means, each of which are well known in the art.

In either of the above embodiments, the amplification reaction will involve a series of steps. The reaction may be either a two step process [i.e. 1) hybridization/extension/ligation followed by 2) denaturation] or a three step process [1] hybridization; 2) extension/ligation and 3) denaturation). These steps may be carried out manually, but they are preferably conducted in an automated thermal cycler.

Hybridization is generally conducted at a temperature of approximately 50°–75° C. for a period of 0.5–2 minutes, more preferably at 60°–70° C. for a period of 1–1.5 minutes, and most preferably at about 63°–68° C. for about 1 minute. The extension/ligation or the hybridization/extension/ligation steps are generally conducted at a temperature of approximately 60°–80° C. for a period of 0.5–5 minutes, more preferably at 68°–78° C. for a period of 2–4 minutes.

The conditions and reagents which make possible the preferred enzymatic ligation step are generally known to those of ordinary skill in the art and depend directly on the type of ligase used. The "ligating enzyme" may be any enzyme known in the art to ligate nucleic acid sequences, including T4 ligase, but it is preferably a ligase stable at temperatures of approximately 0°–95° C., such as AMPLIGASE (Epicentre Technologies, Madison Wis.), Taq ligase (New England Biolabs, Beverly, Mass.) and Pfu ligase (Stratagene, La Jolla, Calif.). Absent a thermally stable ligase, the ligase must be added again each time the cycle is repeated. Approximately at least 5 units of ligating enzyme/picomole of oligonucleotide is used. One unit is defined as the amount required to catalyze the ligation of 50% of the cos sites in one microgram of BstE II digested bacteriophage λ DNA in a total volume of 50 µl in fifteen minutes at 45° C.

The "polymerase" may be any enzyme capable of polymerizing an RNA or DNA strand, including E. coli DNA polymerase I, the Klenow fragment of E. coli DNA polymerase I, AmpliTaq DNA polymerase Stoffel fragment, T4 DNA polymerase, Hot Tub DNA polymerase (Amersham Corp.), Tth DNA polymerase (Epicentre Technologies), Tfl DNA polymerase (Epicentre Technologies), Pfu and Exo-Pfu DNA Polymerase (Stratagene), RNA polymerase or reverse transcriptase. In general, the primer is extended by the polymerase in a target dependent manner, for example, under conditions such that a nucleic acid strand is formed complementary to the nucleic acid sequence to which the primer is hybridized. Preferably, the polymerizing enzyme is stable at temperatures of approximately 0°–95° C., such as Taq DNA polymerase (Perkin-Elmer Corporation, Norwalk, Conn.). Absent a thermally stable polymerase, the polymerase must be added again each time the cycle is repeated. At least approximately 0.5 units of polymerizing enzyme (as defined by the manufacturer)/picomole of oligonucleotide is used.

Extension of a primer by polymerase or transcriptase proceeds in a 5' to 3' direction and requires the addition in adequate amounts of at least the four nucleotide bases in the reaction mixture.

After extension of the primers, it is necessary to separate the nucleic acid strands. The strand separation can be accomplished by any suitable denaturing method including well-known physical, chemical or enzymatic means. For example, one physical method of separating the strands of the nucleic acid involves heating the nucleic acid until it is completely denatured. Typical heat denaturation is generally conducted at a temperature of approximately 85°–110° C., more preferably at 90°–100° C., and most preferably at about 92°–96° C. for a period of at least about 0.5 minutes. One skilled in the art would understand how to modify the temperatures and times so as to optimize the results obtained with different oligonucleotide primers. Alternatively, denaturation can be achieved by other methods known in the art. One such method is by the introduction of a nucleic acid-unwinding enzyme such as helicase.

The reaction is stopped by any method known in the art, such as with a buffer containing a high percentage of denaturant such as formamide, EDTA or by freezing. The products can then be analyzed by any method, but electrophoresis on a polyacrylamide gel is preferable. Preferably, the samples are boiled before loading on the gel to eliminate any secondary structures. The gel may then be dried and placed against autoradiographic film or phosphor screen when the oligonucleotides or amplified strands contain radioactive nuclides. The gel may also be blotted and probed with a probe specific to the region amplified.

The primer may be labeled with a detectable marker by any method known in the art. A preferred method for labeling primers is by end labeling. Primers may be labeled during chemical synthesis by substitution of the $^{31}$P atoms in the phosphate groups with $^{32}$P. The substituted nucleotide may be directly labeled or contain a linker arm for attaching a label, or may be attached to a hapten or other molecule to which a labeled binding molecule may bind (Boehringer Mannheim, Indianapolis, Ind.). Suitable direct labels include radioactive labels such as $^{32}$P, $^{3}$H, and $^{35}$S and non-radioactive labels such as fluorescent markers, such as fluorescein, Texas Red, AMCA blue, lucifer yellow, rhodamine, and the like; cyanin dyes which are detectable with visible light; enzymes and the like. Fluorescent markers may alternatively be attached to nucleotides with activated linker arms. Primers may be indirectly labeled by the methods disclosed above, by incorporating a nucleotide covalently linked to a hapten or other molecule such as biotin or digoxygenin, and performing a sandwich hybridization with a labeled antibody directed to that hapten or other molecule, or in the case of biotin, with avidin conjugated to a detectable label. Antibodies and avidin may be conjugated with a fluorescent marker, or with an enzymatic marker such as alkaline phosphatase or horseradish peroxidase to render them detectable. Conjugated avidin and antibodies are commercially available from companies such as Vector Laboratories (Burlingame, Calif.) and Boehringer Mannheim (Indianapolis, Ind.).

The enzyme can be detected through a colorimetric reaction by providing a substrate and/or a catalyst for the enzyme. In the presence of various catalysts, different colors are produced by the reaction, and these colors can be visualized to separately detect multiple probes. Any substrate and catalyst known in the art may be used. Preferred catalysts for alkaline phosphatase include 5-bromo-4-chloro-3-indolylphosphate (BCIP) and nitro blue tetrazolium (NBT). The preferred substrate for horseradish peroxidase is diaminobenzoate (DAB).

The following examples are presented in order to more fully illustrate the preferred embodiments of the invention. They should in no way be construed, however, as limiting the broad scope of the invention.

| Abbreviations: | |
| --- | --- |
| ATP | adenosine triphosphate |
| dATP | deoxyadenosine triphosphate |
| CTP | cytidine triphosphate |
| dCTP | deoxycytidine triphosphate |
| GTP | guanosine triphosphate |
| dGTP | deoxyguanosine triphosphate |

-continued

| Abbreviations: | |
| --- | --- |
| dTTP | thymidine triphosphate |
| UTP | uridine triphosphate |
| NTP | nucleoside triphosphate |
| nmole (nM) | nanomole |
| pmole (pM) | picomole |
| mmole (mM) | millimole |
| (µM) | micromole |
| ng | nanogram |
| µg | microgram |
| bis | bisacrylamide (N, N'-methylenebis-acrylamide) |
| 5' | the 5' position in the pentose |
| 3' | the 3' position in the pentose |

EXAMPLE 1

Preparation of Target DNA

A 889 basepair region of the multidrug resistance gene (MDR-1) (FIG. 4, SEQ ID NO:1) was selected as a target DNA for the system. The MDR-1 gene is available from the American Type Culture Collection, ATCC No. 65704. The target DNA was prepared by the standard polymerase chain reaction with Primer A (SEQ ID. NO: 2) 5'-
AGGTTAGTAC CAAAGAGGCT CTGG-3'
and
Primer B (SEQ ID NO: 3) 5'-
ACTAACAGAA CATCCTCAAA GCTC-3' based on the known sequence of the gene. The PCR reaction mixture comprised 1 mM Tris HCl (pH 8.4), 5 mM KCl, 1.2 mM MgCl$_2$, 0.8 mM of each dNTP, 1 µM of Primer A, 1 µM of Primer B, 1 ng of template DNA, 2.5 units of Amplitaq™ DNA polymerase (Perkin Elmer Cetus Corporation, Norwalk, Conn.). The reaction mixture was heated at 94° C. for 6 min., and then put through the following cycle 30 times: 94° C. for 1 min, 65° C. for 45 sec., and 72° C. for 3 min. The final polymerization was done at 72° C. for 10 min.

20 µg of DNA was digested with 40 units of RsaI restriction endonuclease at 37° C. for 2 hours under the conditions recommended for the enzyme. An aliquot was run on an agarose gel to confirm that the DNA was completely digested. DNA was then extracted sequentially with equal volumes of phenol, phenol-chloroform (1:1) and chloroform, and then precipitated with two volumes of ethanol. The DNA pellet was suspended in deionized water and the concentration determined by measuring the optical density at 260 nm.

EXAMPLE 2

Preparation of Oligonucleotides

Deoxynucleotide oligomers were synthesized on Milligen/Biosearch Cyclone Plus DNA Synthesizers [Millipore Corporation, Bedford, Mass.] using beta-cyanoethyl phosphoramidite chemistry. All reagents for oligonucleotide synthesis were purchased from Millipore Corporation [Bedford, Mass.].

Oligonucleotides having the following sequences were synthesized:

Oligo 1 (SEQ ID NO. 4):
5' CAACATTTTC ATTTCAACAA CTCC 3'
Oligo 2 (SEQ ID NO. 5):

```
5' TTCTTTCTTA TCTTTCAGTG CTTGTCCAGA 3'
Oligo 3 (SEQ ID NO. 6):
5' GGAGTTGTTG AAATGAAAAT GTTGTC 3'
```

After the specified sequence had been assembled, a 60 minute room temperature treatment with ammonium hydroxide was used to cleave the oligonucleotide from the support. The oligonucleotide was incubated with ammonium hydroxide at 55° C. overnight treatment to remove the protecting groups. Ammonium hydroxide was evaporated to dryness in a Speedvac Concentrator [Savant Instruments, Inc., Farmingdale, N.Y.]. The oligonucleotide was suspended in deionized water and extracted three times with an equal volume of water-saturated N-butanol. Any traces of N-butanol left were removed by evaporation in a Speedvac Concentrator. The concentration of oligonucleotide was determined by measuring optical density at 260 nm in a spectrophotometer.

EXAMPLE 3

Phosphorylation of oligonucleotides

Each oligonucleotide was phosphorylated at the 5' end with ATP and T4 polynucleotide kinase. The reaction mixture (100 µl) contained 2 nmoles of each oligonucleotide 50 mM Tris HCl pH 7.6, 10 mM $MgCl_2$, 5 mM DTT, 0.1 mM spermidine hydrochloride, 0.1 mM EDTA, 1 mM ATP and 50 units of T4 polynucleotide kinase (GIBCO BRL, Gaithersburg, Md.). After 1 hour at 37° C., the enzyme was inactivated by heating at 65° C. for 10 minutes.

EXAMPLE 4

$^{32}$P Labeling of oligonucleotides

Oligonucleotides (20 pmoles) were labeled with $^{32}$P at their 5' end in 60 µl of 50 mM Tris HCl pH 7.6, 10 mM $MgCl_2$, 5 mM DTT, 0.1 mM spermidine hydrochloride, 0.1 mM EDTA and 200 µCi of [γ-$^{32}$P] ATP (3000 Ci/mmole=67 pmoles of ATP; NEN Research Products Div. of Dupont, Boston, Mass.). The reaction was started by adding 20 units of T4 polynucleotide kinase (GIBCO BRL, Gaithersburg, Md.) and incubated at 37° C. for 1 hour. T4 polynucleotide kinase was heat inactivated at 65° C. for 10 minutes.

EXAMPLE 5

Amplification of DNA

Oligonucleotides 1, 2 and 3 at a final concentration of 0.2 µM were incubated in the presence or absence of target DNA (0.5 fmole=$3\times10^8$ molecules) in 20 µl of 25 mM Tris HCl pH 8.0, 10 mM KCl, 2 mM $MgCl_2$, 10 mM DTT, 2 mM $NAD^+$ and 50 µM of dATP, dGTP, dCTP and dTTP. The stock solution of dNTP's was maintained at −20° C.

Three different experiments were performed. In each case, only one oligonucleotide was labeled. 15 units of Taq ligase (New England Biolabs, Beverly, Mass.) and 1 unit of Amplitaq™ DNA Polymerase (Perkin-Elmer Corporation, Norwalk, Conn.) were added and the mixture was overlaid with a drop of mineral oil. Reactions were incubated in a single reaction medium in an Ericomp™ Thermal Cycler (Ericomp Incorporation, San Diego, Calif.) at 94° C. for 6 minutes. The reaction mixture was incubated for 1 minute at 94° C., and 4 minutes at 65° C., with this cycle being repeated 30 times.

The product formation was followed independently using each $^{32}$P-labeled oligonucleotide. The reaction was stopped by adding 13 µl of stop solution (95% formamide, 20 mM EDTA, 0.05% bromophenol blue, 0.05% xylene cyanol FF). Samples were stored at −20° C. until analyzed by electrophoresis.

EXAMPLE 6

Separation of the amplification products

The products of the amplification reaction were separated on an 8% polyacrylamide gel (acrylamide:bis; 19:1) containing 8M urea in 100 mM Tris Borate pH 8.3, 2 mM EDTA. A BRL sequencing gel apparatus model S2 (BRL, Gaithersburg, Md.) was used to run the gel.

Samples (4 µl) were denatured by boiling before loading on the gel. Electrophoresis was performed at a constant 60 watts for 2 hours. The gel was dried and exposed to a Phospho Screen™ (Molecular Dynamics, Sunnyvale, Calif.) and analyzed by a Phosphor Imager™ (Molecular Dynamics, Sunnyvale, Calif.).

Figure 2:
FIG. 2 is a printout from a Phosphor Imager of a scanned acrylamide gel. The arrow indicates the resulting higher molecular weight amplification products.

FIG. 2 is a printout from a Phosphor Imager scan of the samples amplified by the method described in Example 5. In Lane 1 the reaction mixture contained labeled Oligo 1 and unlabeled Oligo 2 and 3. In Lane 2 the reaction mixture was the same as in Lane 1 with the addition of target DNA. The amplified DNA band is indicated with an arrow. In Lane 3 the reaction contained labeled Oligo 2 and unlabeled Oligo 1 and 3. In Lane 4 the reaction mixture was the same as for Lane 3 with the addition of target DNA. In Lane 5 the reaction mixture contained unlabeled Oligo 1 and 2 and labeled Oligo 3. In Lane 6, the reaction mixture was the same as in Lane 5 with the addition of target DNA. It can be seen that amplification does not occur in the absence of the target DNA and that amplification can be detected by labeling any of the oligonucleotides.

EXAMPLE 7

Embodiment 2

Deoxynucleotides are synthesized on Milligen/Biosearch Cyclone Plus™ DNA synthesizers (Millipore Corporation, Bedford Mass.) using beta-cyanoethyl phosphoramidite chemistry as described in Example 2. The synthesis of oligonucleotides 1 and 3 was previously described in Example 2.

Oligonucleotides having the following sequences are synthesized:

```
Oligo 4 (SEQ ID NO: 7)
5' GTTCGGAAGT TTTCTATTGC TTCAGTAGCG 3'
Oligo 5 (SEQ ID NO: 8)
5' CTACTGAAGC AATAGAAAAC TTCCGAAC 3'
```

The oligonucleotides are either phosphorylated at the 5' end with ATP and T4 polynucleotide kinase as described in Example 3 or labeled with $^{32}$P at their 5' end as described in Example 4.

The target DNA is prepared as described in Example 1. Phosphorylated oligonucleotides at a final concentration of 0.2 µM are incubated in the presence of target DNA (0.5 fmole=$3\times10^8$ molecules) in 20 µl of 25 mM Tris HCl pH 8.0, 10 mM KCl, 2 mM $MgCl_2$, 10 mM DTT, 2 mM $NAD^+$ and 50 µM of dATP, dCTP, dGTP and dTTP. The stock solution of dNTP's are maintained at −20° C.

15 units of Taq ligase (New England Biolabs, Beverly, Mass.) and 1 unit of Amplitaq™ DNA polymerase (Perkin-Elmer Corporation, Norwalk, Conn.) are added and the mixture is overlaid with a drop of mineral oil. Reactions are incubated in a single reaction medium in an Ericomp Thermal CyCler™ (Ericomp Incorporation, San Diego, Calif.) at 94° C. for 6 minutes. Then the reaction mixture is incubated for 1 minute at 94° C., and 4 minutes at 65° C., with this cycle being repeated 30 times.

The reaction is stopped by adding 13 μl of stop solution (95% v/v formamide, 20 mM EDTA, 0.05% w/v bromophenol blue, 0.05% w/v xylene cyanol FF). Samples are stored at −20° C. until analyzed by electrophoresis.

The products of the amplification reaction are separated as described in Example 6.

EXAMPLE 8

This example shows the FIG. 12 embodiment of the present invention which uses three primers, with a gap between the first and second primers.

Deoxynucleotides are synthesized on Milligen/Biosearch Cyclone Plus™ DNA synthesizers (Millipore Corporation, Bedford Mass.) using beta-cyanoethyl phosphoramidite chemistry as described in Example 2. Oligonucleotides having the following sequences are synthesized:

Oligo 5 (second primer) (SEQ ID NO: 9):
5' CGCCAGGGTT TTCCCAGTCA CGAC 3'
Oligo 6 (first primer) (SEQ ID NO: 10):
5' CGTAATCATG GTCATAGCTG TTTCCTG-$NH_2$ 3'
Oligo 7 (third primer) (SEQ ID NO: 11):
5' GGAAACAGCT ATGACCATGA TTACGA 3'

M13mp18 phage single and double stranded DNA was obtained from New England Biolabs, Beverly, Mass. and used as a target in this example. Its sequence is well known, and the relevant portion from nucleotides 6201 to 6340 is as follows (SEQ ID NO:12):

| 6201 | CACACAGGAA | ACAGCTATGA | CCATGATTAC | GAATTCGAGC | TCGGTACCCG |
| 6251 | GGGATCCTCT | AGAGTCGACC | TGCAGGCATG | CAAGCTTGGC | ACTGGCCGTC |
| 6301 | GTTTTACAAC | GTCGTGACTG | GGAAAACCCT | GGCGTTACCC | |

Oligo 5 is complementary to nucleotides 6311–6334; oligo 6 is complementary to nucleotides 6205–6231. Oligos 5 and 7 at a final concentration of 0.25 μM, and phosphorylated oligo 6 at a final concentration of 0.5 μM were incubated in the presence of M13mp18 double stranded DNA (present at $2.5\times10^{-13}$M) in 20 μl of 50 mM Tris HCl pH 8.0, 10 mM DTT, 2 mM NAD, 10 mM KCl, 4 mM $MgCl_2$, 20 μM dATP, dGTP, dTTP and 5 μM dCTP. Three different sets of assays were set up. In each case, only one 5'-$^{32}$P labelled oligonucleotide was added. Thus, in the first case, only oligo 5 was labelled. In the second case, only oligo 6 was labelled. In the third case, only oligo 7 was labelled. Further, for each assay, a negative control was run using the same reagents except that target DNA was absent. Five units of AmpliTaq Stoffel fragment and 30 units of Taq ligase were added. Reaction tubes were incubated in GeneAmp™ PCR system 9600 thermal cycler (Perkin Elmer Cetus) at 94° C. for 2 minutes (1 cycle) and then 94° C. for 1 minute and 55° C. for 2.5 minutes (30 cycles).

The reaction was stopped by adding stop solution (95% formamide, 20 mM EDTA, 0.05% bromophenol blue, 0.05% xylene cyanol FF). The products of the amplification reaction were analyzed on an 8% polyacrylamide denaturing gel. The results are shown in FIG. 5, which is a printout from a Phosphor Imager scan of the samples amplified in this example. In lane 1 the reaction mixture contained $^{32}$P-labeled oligo 5 and unlabelled oligo 6 and 7. In lane 2 the reaction mixture was the same as in lane 1 with the addition of target DNA. The amplified DNA band is indicated with an arrow. In lane 3 the reaction mixture contained $^{32}$P-labeled oligo 6 and unlabelled oligo 5 and 7. In lane 4 the reaction mixture was the same as in lane 3 with the addition of target DNA. In lane 5 the reaction mixture contained $^{32}$P-labeled oligo 7 and unlabelled oligo 5 and 6. In lane 6 the reaction mixture was the same as in lane 5 with the addition of target DNA. It can be seen that the amplification does not occur in the absence of the target DNA and that amplification product can be detected by labeling any one of the three oligonucleotides.

EXAMPLE 9

Figure 3:
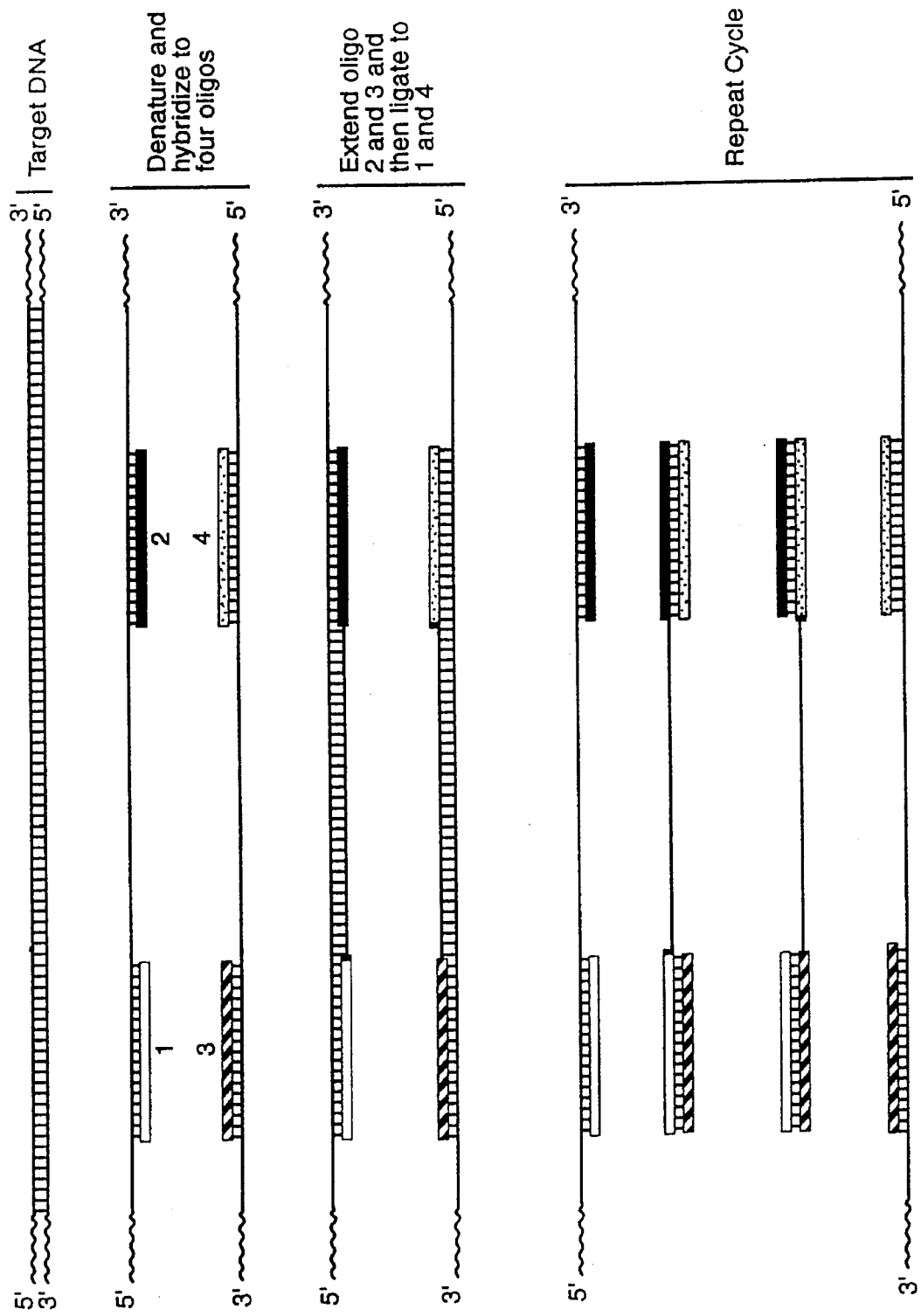
FIG. 3 depicts another embodiment of the method of DNA amplification/detection as set forth herein.

This example shows the FIG. 3 embodiment of the present invention which uses four primers, two of which are extended.

Deoxynucleotides are synthesized on Milligen/Biosearch Cyclone Plus™ DNA synthesizers (Millipore Corporation, Bedford Mass.) using beta-cyanoethyl phosphoramidite chemistry as described in Example 2. The synthesis of oligonucleotides 5, 6 and 7 was previously described in Example 8. An oligonucleotide having the following sequence is synthesized:

Oligo 8 (SD6) (SEQ ID NO: 13):
5' CGTGACTGGG AAAACCCTGG CGTT-Cordycepin 3'

Oligos 5 and 7 (the second and third primers, respectively) at a final concentration of 0.025 μM and phosphorylated oligos 6 and 8 (first and fourth primers, respectively) at a final concentration of 0.05 μM were incubated in the presence of M13mp18 phage double stranded DNA (2.5× $10^{-13}$M) in 20 μl of 50 mM TrisCl pH 8.0, 10 mM DTT, 2 mM NAD, 10 mM KCl, 4 mM $MgCl_2$, 20 μM dATP, dGTP, dTTP and 5 μM dCTP. Four different sets of assays were set up. In each case, only one 5'-$^{32}$P labelled oligonucleotide was added. Further, for each assay, a negative control was run using the same reagents without target DNA. Five units of AmliTaq stoffel fragment and 30 units of Taq ligase were added. Reaction tubes were incubated in GeneAmp™ PCR system 9600 thermal cycler (Perkin Elmer Cetus) at 94° C. for 2 minute (1 cycle) and then 94° C. for 1 minute and 55° C. for 2.5 minutes (30 cycles).

Figure 6:
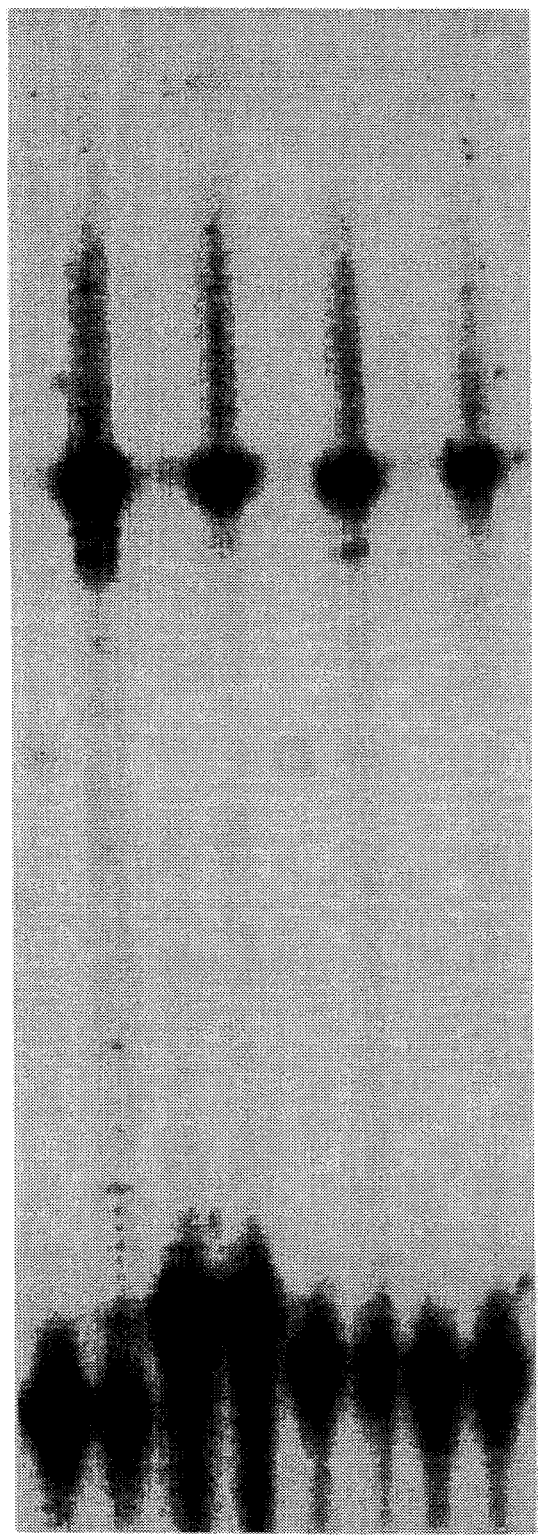

The reaction was stopped by adding stop solution as in Example 8. The products of the amplification reaction were analyzed on an 8% polyacrylamide denaturing gel. The results are shown in FIG. 6, which is a printout from a Phosphor Imager scan of the samples amplified in this example. In lane 1 the reaction mixture contained $^{32}$P-labeled oligo 5 and unlabelled oligo 6, 7 and 8. In lane 2 the reaction mixture was the same as in lane 1 with the addition of target DNA. The amplified DNA band is indicated with an arrow. In lane 3 the reaction mixture contained $^{32}$P-labeled oligo 6 and unlabelled oligo 5, 7 and 8. In lane 4 the reaction mixture was the same as in lane 3 with the addition of target DNA. In lane 5 the reaction mixture contained $^{32}$P-labeled oligo 7 and unlabelled oligo 5, 6 and 8. In lane 6 the reaction mixture was the same as in lane 5 with the addition of target DNA. In lane 7 the reaction mixture contained $^{32}$P-labeled oligo 8 and unlabelled oligo 5, 6 and 7. In lane 8 the reaction mixture was the same as in lane 7 with the addition of target DNA. It can be seen that the amplification does not occur in the absence of the target DNA and that amplification product can be detected by labeling any one of the four oligonucleotides.

EXAMPLE 10

This example shows that increasing the salt concentration and decreasing the nucleotide concentration will decrease the strand displacement activity by DNA polymerase and promote ligation by DNA ligase. Extension of a 5'-$^{32}$P end labelled primer (oligo 5 from Example 8) annealed to M13mp18 single stranded DNA was monitored in the presence of another primer (oligo 6 from Example 8) which annealed 79 nucleotides down stream of oligo 5. The extension of blocking primer (oligo 6) by DNA polymerase was prevented by incorporating a NH$_2$-group at the 3' end.

Under the assay conditions, oligo 5 was extended by DNA polymerase until it reached the 5' end of oligo 6. The extended products accumulated for some time and then the extension continued beyond the blocking primer (oligo 6). When DNA ligase was present in the assay the extended products at the 5' end of oligo 6 accumulated long enough to be ligated to oligo 5.

A. Assay conditions for strand displacement by DNA polymerase

5'-$^{32}$P end labelled primer (oligo 5) (15 nM) and blocking primer (oligo 6) (300 nM) were simultaneously annealed to M13mp18 phage single stranded DNA (26 nM). Annealing was performed in 10 mM TrisCl pH 7.5, 10 mM mgCl$_2$ and 50 mM NaCl, by heating at 95° C. for 3 minutes followed by slow cooling to room temperature.

Strand displacement by AmpliTaq DNA polymerase was assayed by diluting the primer template complex ten fold in OCR buffer (50 mM Tris HCl pH 8.0, 10 mM DTT, 2 mM NAD), 100 mM KCl, 2 mM MgCl$_2$, 25 units/ml of AmpliTaq DNA polymerase and appropriate concentrations of deoxynucleotide triphosphates as described below. Assays using AmpliTaq DNA polymerase Stoffel fragment were performed under same conditions except 10 mM KCl and 50 units/ml of enzyme. The reaction was incubated at 55° C. and aliquots were taken after 30 seconds, 1 and 2 minutes. Stop solution was added and samples were analyzed on 8% polyacrylamide denaturing gel.

B. Assay conditions for strand displacement by DNA polymerase in presence of DNA ligase The assay were performed as in part A above except that the blocking primer was phosphorylated at the 5' end and 1500 units/ml of Taq ligase (New England Biolabs) were also added. The results of both assays A and B are shown in FIGS. 7–10.

Figure 7:
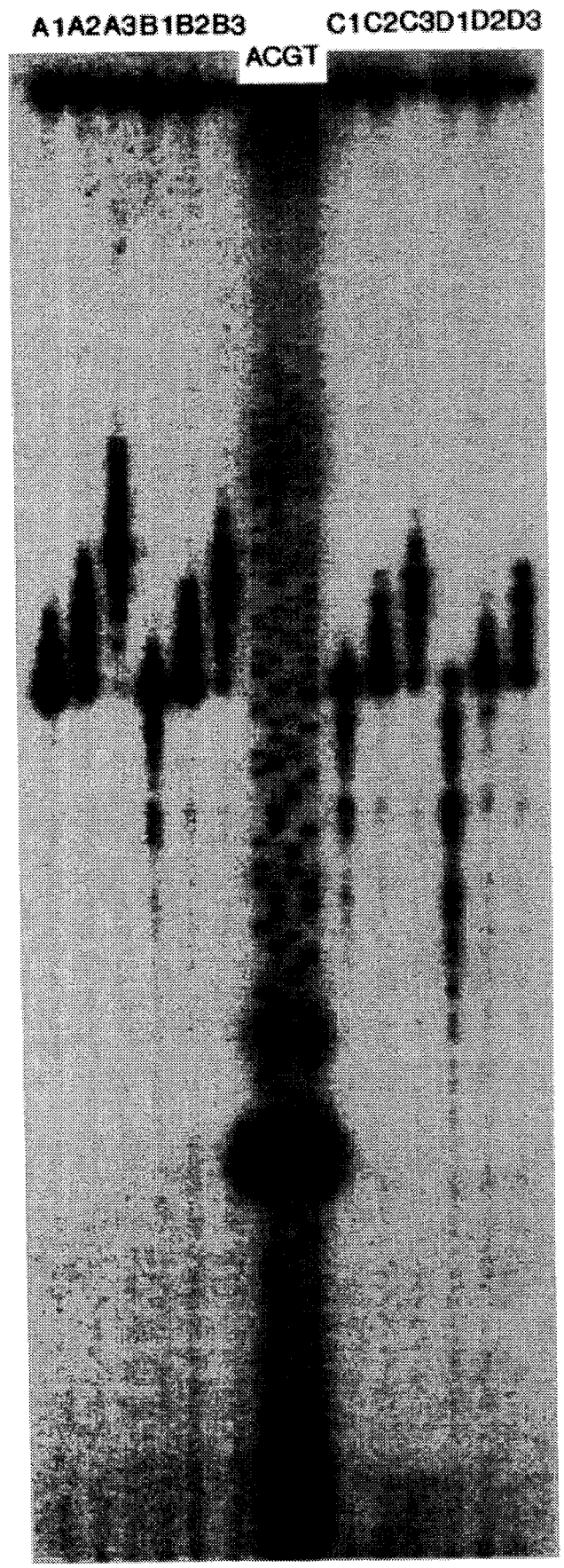

FIG. 7 shows the strand displacement by AmpliTaq DNA polymerase in presence of 100 mM KCl. The lanes are as follows:

| Lanes A1–A3: | 20 µM all four dNTP's. |
| Lanes B1–B3: | 20 µM dA, dG, dT and 4 µM dC |
| Lanes C1–C3: | 20 µM dA, dG, dT and 2 µM dC |
| Lanes D1–D3: | 20 µM dA, dG, dT and 1 µM dC |

Lanes A, C, G, T display the dideoxy sequencing pattern from the oligo 5 primer and M13mp18 phage DNA. The arrow points to the position where the 5' end of blocking primer (oligo 6) binds. Lanes 1, 2, 3 are 30 seconds, 1 minute and 2 minute time points, respectively.

Figure 8:

FIG. 8 shows the strand displacement by AmpliTaq Stoffel fragment DNA polymerase in presence of 10 mM KCl. The lanes are as follows:

| Lanes A1–A3: | 20 µM all four dNTP's |
| Lanes B1–B3: | 20 µM dA, dG, dT and 10 µM dC |
| Lanes C1–C3: | 20 µM dA, dG, dT and 5 µM dC |

Lanes A, C, G, T display the dideoxy sequencing pattern from the oligo 5 primer and M13mp18 phage DNA. The arrow points to the position where the 5' end of blocking primer (oligo 6) binds. Lanes 1, 2, 3 are 30 seconds, 1 minute and 2 minute time points, respectively.

Figure 9:
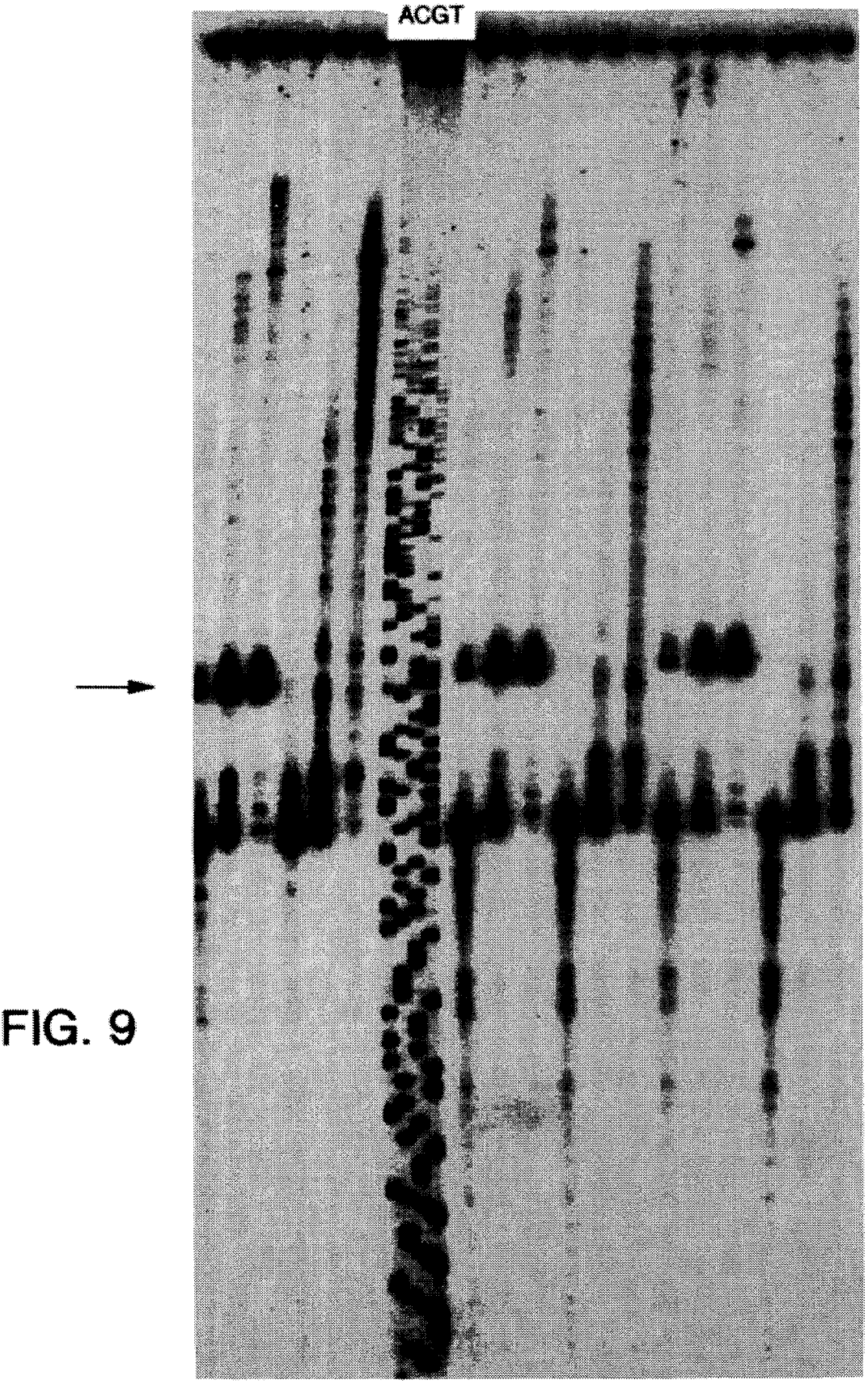

FIG. 9 shows the strand displacement by AmpliTaq DNA polymerase in presence of 100 mM KCl and Taq ligase. The lanes are as follows:

| Lanes A1–A3; B1–B3: | 20 µM all four dNTP's |
| Lanes C1–C3; D1–D3: | 20 µM dA, dG, dT and 4 µM dC |
| Lanes E1–E3; F1–F3: | 20 µM dA, dG, dT and 2 µM dC |
| Lanes B1–B3, D1–D3 and F1–F3 had no ligase | |

Lanes A, C, G, T display the dideoxy sequencing pattern from the oligo 5 primer and M13mp18 phage DNA. The arrow points to the position of the product formed by the ligation of extended primer (oligo 5) and oligo 6. Lanes 1, 2, 3 are 30 seconds, 1 minute and 2 minute time points, respectively.

Figure 10:
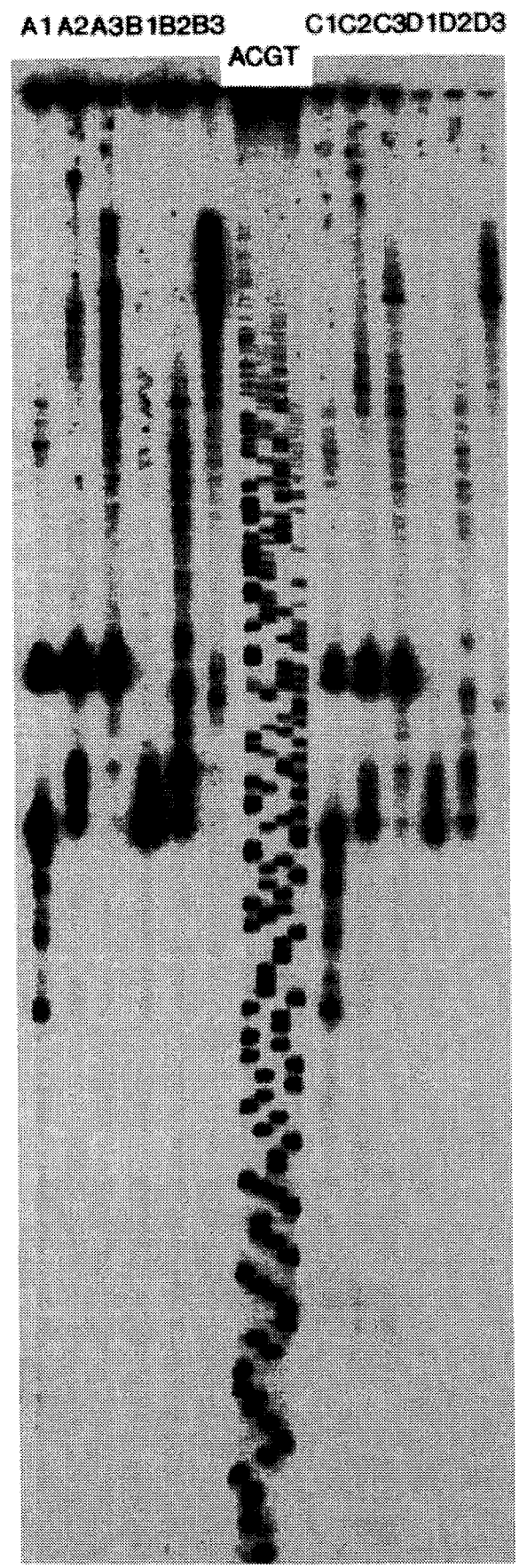

FIG. 10 shows the strand displacement by AmpliTaq Stoffel fragment DNA polymerase in presence of 10 mM KCl and Taq ligase. The lanes are as follows:

| Lanes A1–A3; B1–B3: | 20 µM all four dNTP's |
| Lanes C1–C3; D1–D3: | 20 µM dA, dG, dT and 10 µM dC |
| Lanes B1–B3 and D1–D3 had no ligase | |

Lanes A, C, G, T display the dideoxy sequencing pattern from the oligo 5 primer and M13mp18 phage DNA. The arrow points to the position of the product formed by the ligation of extended primer (oligo 5) and oligo 6. Lanes 1, 2, 3 are 30 seconds, 1 minute and 2 minute time points, respectively.

It is clear from FIGS. 7–10 that using high salt and decreasing the concentration of the nucleotide at the 5' end of oligo 6 (which in this particular example is dCTP), oligo 5 was extended by DNA polymerase until it reached the 5' end of oligo 6. The extended products accumulated for long enough time to be ligated to oligo 6 by DNA ligase. AmpliTaq polymerase is about ten times more processive than Stoffel fragment. Therefore it requires higher salt concentration and lower dCTP concentration to achieve a similar degree of processivity as compared to Stoffel fragment.

EXAMPLE 11

This example shows the FIG. 1 embodiment of the present invention which uses three primers and no gap.

Deoxynucleotides are synthesized on Milligen/Biosearch Cyclone Plus™ DNA synthesizers (Millipore Corporation, Bedford Mass.) using beta-cyanoethyl phosphoramidite chemistry as described in Example 2. The synthesis of oligonucleotide 3 was previously described in Example 2.

Oligonucleotide having the following sequences are synthesized:

SD4(M)G:
5' GGTAATCATG GTCATAGCTG TTTCCTG 3' (SEQ ID NO: 19)
Oligo 5:
5' CGCCAGGGTT TTCCCAGTCA CGAC 3' (SEQ ID NO: 9)
63 mer template (control):
5' GGAAACAGCT ATGACCATGA TTACCAATTC GAGCTCCGTC GTGACTGGGA
AAACCCTGGC GTT 3' (SEQ ID NO: 20)
63 mer template (N = Ara C):
5' GGAAACAGCT ATGACCATGA TTACNAATTC GAGCTCCGTC GTGACTGGGA
AAACCCTGGC GTT 3' (SEQ ID NO: 21)
63 mer template (N = O-methyl C):
5' GGAAACAGCT ATGACCATGA TTACNAATTC GAGCTCCGTC GTGACTGGGA
AAACCCTGGC GTT 3' (SEQ ID NO: 22)
63 mer template (methyl phosphonate linkage):
5' GGAAACAGCT ATGACCATGA TTACCAATTC GAGCTCCGTC GTGACTGGGA
AAACCCTGGC GTT 3' (SEQ ID NO: 23)

Oligo 9 (SEQ ID NO: 14)
5' AACATTTTCA TTTCAACAAC TCCTGC-Phosphate 3'
Oligo 10 (SEQ ID NO: 15)
5' TTTCTTATCT TTCAGTGCTT GTCCAGA- araC 3'

Oligonucleotides 3 and 10 at a final concentration of 0.025 µM and oligo 9 phosphorylated at the 5' end at a final concentration of 0.05 µM were incubated in the presence of target DNA ($5 \times 10^{-12}$M, RsaI digested MDR-1 DNA) in 20 µl of 50 mM Tris HCl pH 8.0, 10 mM DTT, 2 mM NAD, 10 mM KCl, 4 mM $MgCl_2$, 20 µM of dATP, dCTP, dGTP, dTTP. Three different sets of assays were set up. In each case, only one 5'-$^{32}$P labelled oligonucleotide was added. Thus, in the first case, only oligo 9 was labelled. In the second case only oligo 10 was labelled. In the third case, only oligo 3 was labelled. Further, for each assay, a negative control was run using the same reagents except that target DNA was absent. Five units of AmliTaq Stoffel fragment and 30 units of Taq ligase were added. Reaction tubes were incubated in Gene-Amp™ PCR system 9600 thermal cycler (Perkin Elmer Cetus) at 94° C. for 2 minutes (1 cycle) and then 94° C. for 1 minute and 55° C. for 2.5 minutes (30 cycles).

Figure 11:

The reaction was stopped by adding stop solution as in example 5. The products of the amplification reaction were analyzed on an 8% polyacrylamide denaturing gel. The results are shown in FIG. 11, which is a printout from a Phosphor Imager scan of the samples amplified in this example. In lane 1 the reaction mixture contained $^{32}$P-labeled oligo 9 and unlabelled oligo 3 and 10. In lane 2 the reaction mixture was the same as in lane 1 with the addition of target DNA. The amplified DNA band is indicated with an arrow. In lane 3 the reaction mixture contained $^{32}$P-labeled oligo 10 and unlabelled oligo 3 and 9. In lane 4 the reaction mixture was the same as in lane 3 with the addition of target DNA. In lane 5 the reaction mixture contained $^{32}$P-labeled oligo 3 and unlabelled oligo 9 and 10. In lane 6 the reaction mixture was the same as in lane 5 with the addition of target DNA. It can be seen that the amplification does not occur in the absence of the target DNA and that amplification product can be detected by labeling any one of the three oligonucleotides. AraC at the 3' end of oligo 10 does get ligated to the 5' end of oligo 9.

EXAMPLE 12

This example shows that introducing a synthetic modification in the template slows down DNA polymerase and prevents strand displacement. The following deoxyoligonucleotides were synthesized for this experiment.

In the 63 mer template (AraC) (SEQ ID NO:21) the 25th nucleotide (dCMP) from the 5' end was replaced with Ara CMP.

In the 63 mer template (O-methyl C) (SEQ ID N0:22) the 25th nucleotide (dCMP) from the 5' end was replaced with 2'-O-methyl CMP.

In the 63 mer template (methyl phosphonate) (SEQ ID NO:23) the phosphodiester bond between 25th and 26th nucleotide from the 5' end was replaced with a methyl phosphonate bond.

The oligos were synthesized on an Applied Biosystems 394 DNA/RNA Synthesizer. Ara-C-CE Phosphoramidite, 2'-O-Methyl-C-CE Phosphoramidite, and dC-Methyl-Phosphonamidite were purchased from Glen Research, Sterling, Va. and used according to manufacturer's instructions.

Figure 15:
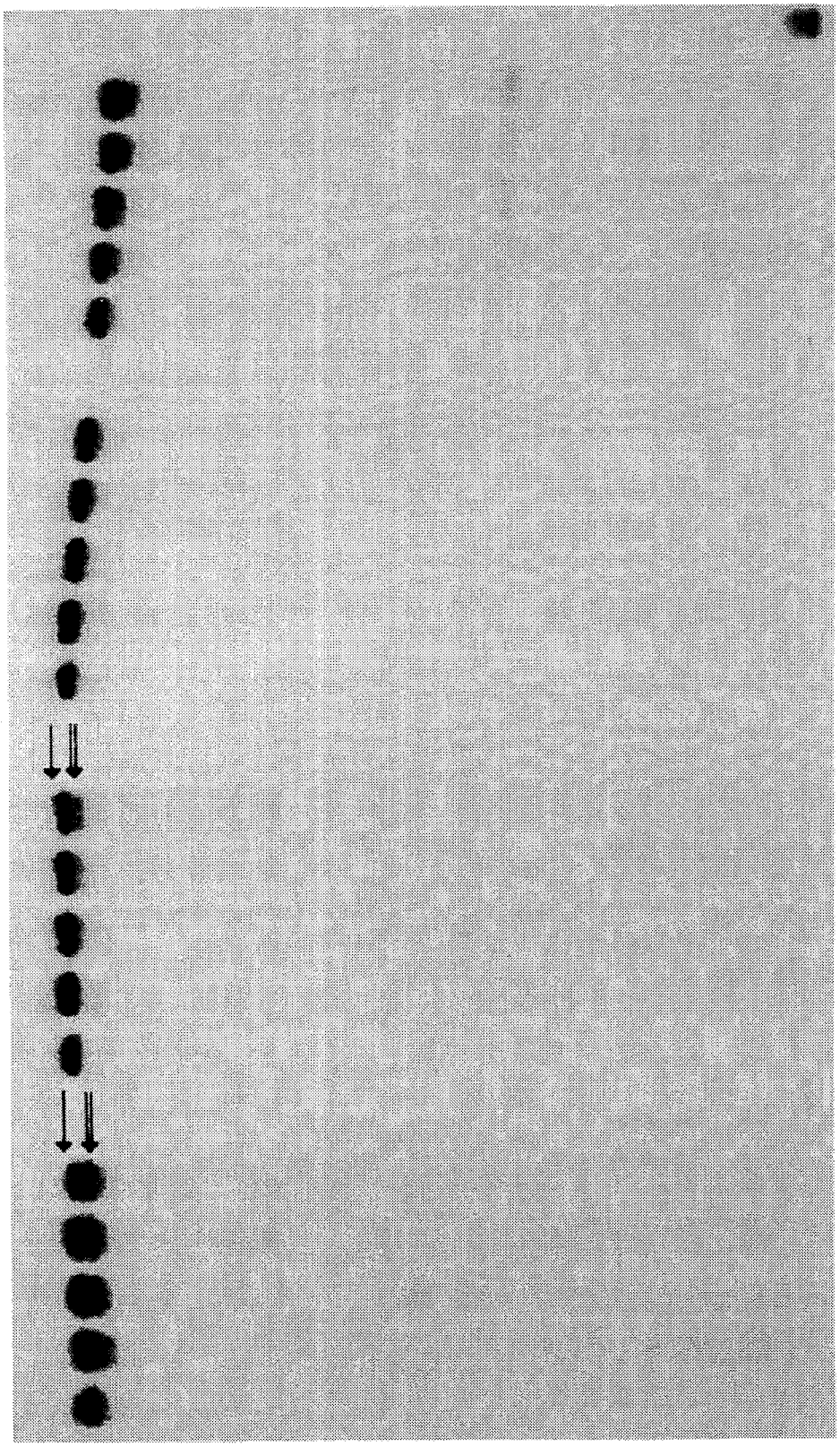
FIG. 15 is a printout from a Phosphor Imager of a scanned acrylamide gel which shows amplification achieved with various embodiments of the present invention.

The general scheme of this example is depicted in FIG. 14. The 63 mer oligo with different modifications was used as the template. A primer (oligo 5) and blocking oligo [SD4(M)G] were simultaneously annealed to the 63 mer oligo (FIG. 15). Extension of 5' $^{32}$P-labelled primer (oligo 5) by increasing the concentration of DNA polymerase was monitored in the presence of DNA ligase. Oligo 5 was extended by DNA polymerase until it reached the 5' end of blocking oligo. The extended product was either ligated by DNA ligase to the 5' end of the blocking oligo or the blocking oligo was displaced and the extension continued to the end of the 63 mer template. It is apparent that if there is no strand displacement and extended primer is ligated to the blocking oligo then the size of the final product should be 63 nucleotides long. But if the blocking oligo is displaced and the primer is extended to the end of the template, then the final product should be 61 nucleotides long. It is evident that compared to the control template, the presence of a modification in the 63 mer oligo template allows DNA polymerase to pause long enough for the DNA ligase to seal the gap and prevent strand displacement.

It has been reported that most template modifications result in arrest of DNA synthesis one nucleotide before the modification site (See Moore & Straus, *Nature*, 278, 664–666 (1979); Moore, et al., *Biochemistry*, 78, 110–114 (1981); Sagher & Strauss, *Biochemistry*, 22, 4518–26 (1983); Takeshita, et al., *J. Biol.Chem.*, 262, 10171–79 (1987)). An exception is the thymine glycol (Clark & Breardsley, *Biochemistry*, 26, 5398–5403 (1987)) and Ara C (Mikita & Beardsley, *Biochemistry*, 27, 4698–4705 (1988)) modifications, which arrest synthesis at the site of modification. All the modifications in DNA we used including AraC indicate that the DNA synthesis one nucleotide before the modification site was arrested long enough for the DNA ligase to seal the nick and prevent strand displacement.

Assay conditions:

5'-$^{32}$P labelled primer (oligo 5) (20 nM) and blocking oligo [SD4(M)G] (400 nM) were mixed with 63 mer oligo (80 nM) in 10 mM TrisCl pH 7.5, 10 mM MgCl$_2$ and 50 mM NaCl. Annealing was performed by heating the mixture to 95° C. for 3 minutes followed by slow cooling to room temperature.

The assay was performed by diluting the annealed primer:template complex ten fold in 25 mM Taps buffer pH 8.75 at 25° C., 10 mM DTT, 5 mM MgAc, 1 mM NAD, 40 mM NH$_4$Ac, 0.1 mg/ml BSA, 0.01% Tritonx100, 2.5% glycerol, 50 μM all four dNTPs, 1250 units/ml of Taq Ligase (New England Biolabs) and indicated units of KlenTaq 1 DNA polymerase (Ab Peptides, Inc. St. Louis, Mo.). The tubes were incubated at 55° C. for one minute. The reaction was stopped by adding stop solution and samples were analyzed on 15% polyacrylamide denaturing gel.

FIG. 15 shows the effectiveness of having a modification in the template on prevention of strand displacement. The lanes are as follows:

| Lane P | $^{32}$P labelled primer (oligo 5) |
| Lane A1, B1, C1, and D1 | $^{32}$P labelled 63 mer template. |
| Lane A2–A5 | synthesis on control template |
| Lane B2–B5 | synthesis on AraC template |
| Lane C2–C5 | synthesis on 2'- O- Methyl C template |
| Lane D2–D5 | synthesis on Methyl Phosphonate template |

Lanes 2, 3, 4 and 5 are 1, 2, 5, and 10 units of KlenTaq 1 DNA polymerase. The dark arrow indicates the position of extended and ligated product (63 mer). The blank arrow indicates the position of full length extended product (61 mer). This shows that a significant amount of strand displacement took place when the unmodified control template was used, whereas no significant strand displacement is evident with the use of the modified template.

EXAMPLE 13

This example illustrates that a modification in the template does not have a significant effect on the nick closing activity of DNA ligase across the modification. FIG. 16 shows the design of the experiment. Oligos SD4(M)G and SD23 were hybridized to 63 mer templates with various modifications. The efficiency of DNA ligase in closing the gap between the 3' end of SD23 and 5' end of SD4(M)G under the present amplification conditions was tested. The synthesis of the 63 mer templates and SD4(M)G has been described in Example 12. Oligo SD23 has the following sequence:

| SD23: |
| 5' ACGACGGAGC TCGAATT 3' (SEQ ID NO: 24) |

Assay conditions:

5' $^{32}$P labelled SD23 (20 nM) and SD4(M)G (400 nM) were mixed with 63 mer templates (80 nM) in 10 mM TrisCl pH 7.5, 10 mM MgCl$_2$ and 50 mM NaCl. Annealing was performed by heating the mixture to 95° C. for 3 minutes followed by slow cooling to room temperature.

The assay was initiated by diluting the annealed primer:template complex ten fold in 25 mM Taps buffer pH 8.75 at 25° C., 10 mM DTT, 5 mM MgAc, 1 mM NAD, 40 mM NH$_4$Ac, 0.1 mg/ml BSA, 0.01% Tritonx100, 2.5% glycerol, 25 units/ml of Taq Ligase (New England Biolabs). The tubes were incubated at 55° C. and aliquots were taken after 30 seconds, one minute, and two minutes. The reaction was stopped by adding stop solution and samples were analyzed on a 15% polyacrylamide denaturing gel.

Figure 17:
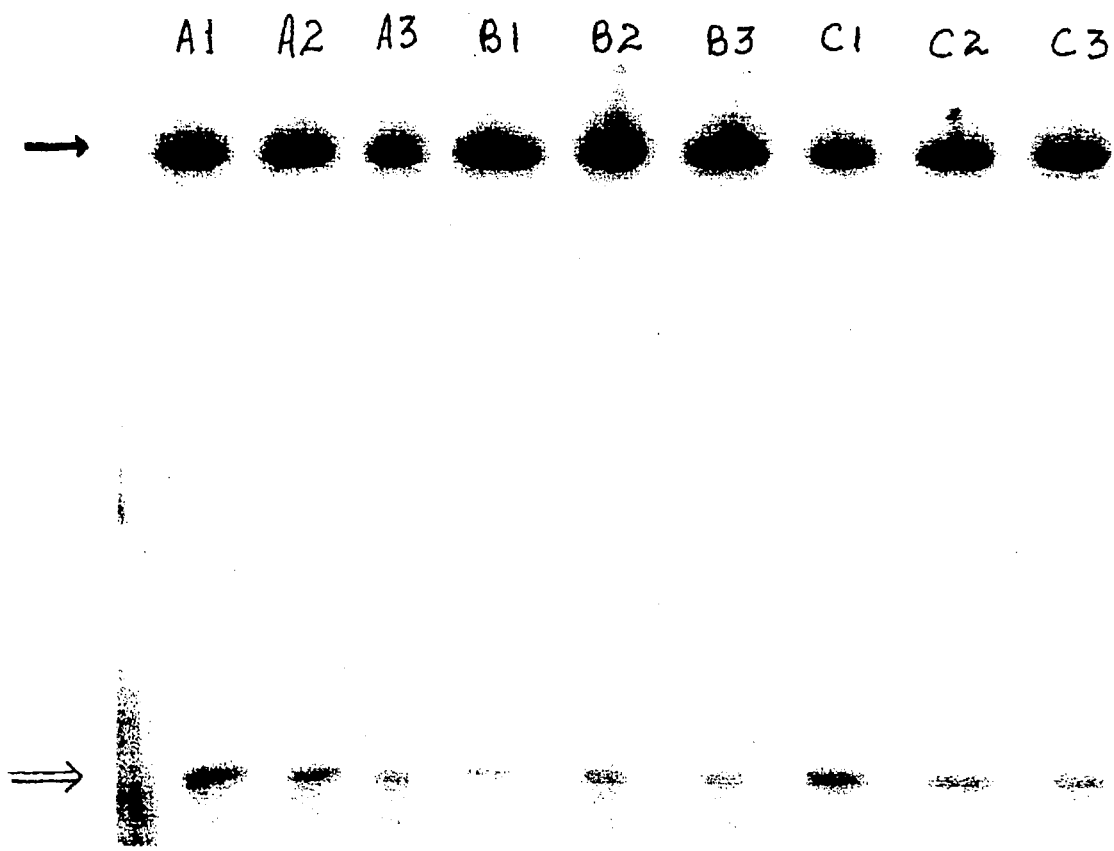
FIG. 17 is a printout from a Phosphor Imager of a scanned acrylamide gel which shows results obtained from the experiment depicted in FIG. 16.

FIG. 17 shows the results of the above experiment. The dark arrow indicates ligated product and the blank arrow points to SD23. Under the present experimental conditions there is no difference between ligation on control template vs modified templates.

| Lanes A1–A3 | ligation on 63 mer control template |
| Lanes B1–B3 | ligation on 63 mer 2'-O-Methyl C template |
| Lanes C1–C3 | ligation on 63 mer Methyl Phosphonate template |

Lanes 1, 2 and 3 are 30 seconds, 1 minute, and 2 minute time points, respectively.

EXAMPLE 14

This example illustrates the effectiveness of using a modification in the oligo on the amplification. The same target described in FIG. 13 was amplified using two sets of oligos. Oligos FGA1 (SEQ ID NO:18), FGA 2 (SEQ ID NO:17) and FGA 3 (SEQ ID NO:16) have been described above. Oligo FGA 4 has the following sequence:

| FGA 4 (SEQ ID NO: 25) (N = AraC) |
| 5' CCATAGGTTT TGAACTCANA G 3' |

FGA 4 has same sequence as FGA 1 except that the third nucleotide from the 3' end is changed from dC to AraC.

Amplification conditions:

Oligonucleotides FGA 2 and FGA 3, or FGA 2 and FGA 4 at a final concentration of 0.25 μM and FGA 1 at a final concentration of 0.5 μM were incubated in the presence of target DNA (100 ng of human placental DNA, Oncor, Inc. Gaithersburg, Md.) in 20 μl of 25 mM Taps buffer pH 8.75 at 25° C., 10mM DTT, 5 mM MgAc, 1 mM NAD, 40 mM NH$_4$Ac, 0.1 mg/ml BSA, 0.01% Tritonx100, 2.5% glycerol, 50 μM of all four dNTPs (dATP, dCTP, dGTP, and dTTP), 40 units of Taq Ligase (New England Biolabs) and 1.0 units of KlenTaq 1 DNA polymerase (Ab Peptides, Inc. St. Louis, Mo.). Reaction tubes were incubated in GeneAmp™ PCR system 9600 thermal cycler (Perkin Elmer Cetus) at 94° C. for 5 minutes (1 cycle) and then 94° C. for 30 seconds and 55° C. for 2.5 minutes (30 cycles). The reaction was stopped by adding stop solution and the amplified products were analyzed on an 6% polyacrylamide denaturing gel. Three different sets of assays were set up. In each case, only one 5'-$^{32}$P labelled oligo was added. A negative control was also run using the same reagents except that target DNA was omitted.

Figure 18:
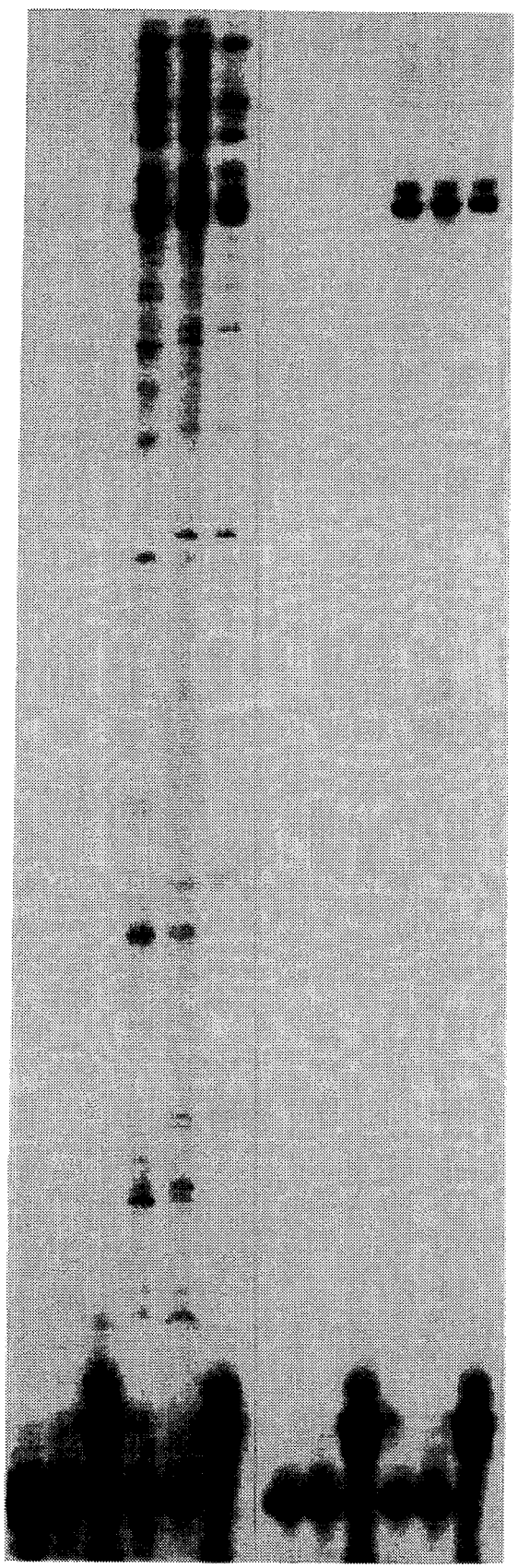
FIG. 18 is a printout from a Phosphor Imager of a scanned acrylamide gel which shows results obtained from the experiment described in Example 14.

The results are shown in FIG. 18, which is a printout from a phosphor imager scan of the gel. In lane 1 the reaction mixture contained $^{32}$P labelled oligo FGA 1 and unlabelled oligo FGA 2 and FGA 3. In lane 2 the reaction mixture contained $^{32}$P labelled FGA 2 and unlabelled FGA 1 and FGA 3. In lane 3 the reaction mixture contained $^{32}$P labelled FGA 3 and unlabelled FGA 1 and FGA 2. In lane 4 the reaction mixture contained $^{32}$P labelled FGA 4 and unlabelled FGA 2 and FGA 3. In lane 5 the reaction mixture contained $^{32}$P labelled FGA 2 and unlabelled FGA 4 and FGA 3. In lane 6 the reaction mixture contained $^{32}$P labelled FGA 3 and unlabelled FGA 4 and FGA 2. The products formed from FGA 1 and FGA 2 should have the same 277 nucleotide length, whereas products from FGA 3 and FGA 4 should be 272 nucleotides long. It is very clear from the results shown in this example that the amplified products obtained from the oligo set having the AraC modification, have no strand displacement.

Although only preferred embodiments of the invention are specifically illustrated and described above, it will be appreciated that many modifications and variations of the present invention are possible in light of the above teachings and within the purview of the appended claims without departing from the spirit and intended scope of the invention.

What is claimed is:

1. A process for amplifying enzymatically a target nucleic acid sequence contained in a nucleic acid or a mixture of nucleic acids while reducing strand displacement by polymerase, comprising the steps of:

a) selecting the target nucleic acid sequence;

b) providing primers, said primers comprising a first primer which is substantially complementary to a first segment at a first end of the target nucleic acid sequence and a second primer which is substantially complementary to a second segment at a second end of the target nucleic acid sequence and whose 3' end is adjacent to the 5' end of the first primer and a third primer which is substantially complementary to at least a portion of said first primer such that when the third primer is hybridized to the first primer, the position of the third primer complementary to the base at the 5' end of the first primer contains a modification which reduces strand displacement under polymerizing conditions;

c) providing at least four different nucleotide bases;

d) hybridizing said first and second primers to the target nucleic acid sequence in a target dependent manner to form a primer-target complex;

e) ligating under conditions such that the adjacent 5' end of the first primer and the 3' end of the second primer will ligate to form a fused amplification product substantially complementary to said target nucleic acid sequence;

f) dissociating said fused amplification product from said target nucleic acid sequence;

g) hybridizing said third primer to said fused amplification product;

h) extending said third primer in the presence of the nucleotide bases under conditions such that an extended amplification product is formed substantially complementary to said fused amplification product and which contains said modification;

i) dissociating the extended amplification product from the fused amplification product;

j) allowing the extended, modified amplification product to hybridize to additional first and second primers in a target dependent manner; and k) ligating the 5' end of the additional first primer to the 3' end of the additional second primer while reducing strand displacement of the additional first primer, to form additional amplification product.

2. The process of claim 1, wherein the modification is to the nucleotide base.

3. The process of claim 2, wherein the modification is a base selected from the group consisting of xanthine, hypoxanthine and an abasic site.

4. The process of claim 1, wherein the modification is to the nucleotide sugar moiety.

5. The process of claim 4, wherein the modification is selected from the group consisting of 2'-O-alkylribonucleotides, ribonucleotides, and arabinosyl nucleotide derivatives.

6. The process of claim 5, wherein the modification is a 2'-O-methylribonucleotide.

7. The process of claim 1, wherein the modification is to the internucleotide linkage.

8. The process of claim 7, wherein the modification is a methyl phosphonate internucleotide linkage.

9. The process of claim 1, wherein the target nucleic acid is single stranded.

10. The process of claim 1, wherein steps (d) through (k) are repeated at least once.

11. The process of claim 1, wherein the target nucleic acid is DNA.

12. The process of claim 1, wherein the target nucleic acid is RNA.

13. The process of claim 1, wherein steps (e) and (k) are conducted in the presence of a ligating enzyme.

14. The process of claim 13, wherein the ligating enzyme is T4 DNA ligase.

15. The process of claim 13, wherein the ligating enzyme is stable at 0°–95° C.

16. The process of claim 15, wherein the ligating enzyme is selected from the group consisting of Taq ligase, Pfu ligase and Ampligase.

17. The process of claim 1, wherein step (h) is conducted in the presence of a polymerase.

18. The process of claim 17, wherein the polymerase is selected from the group consisting of E. coli DNA polymerase I, Klenow fragment of E. coli DNA polymerase I, and T4 DNA polymerase.

19. The process of claim 17, wherein the polymerase is stable at temperatures of 0°–95° C.

20. The process of claim 19, wherein the polymerase is selected from the group consisting of Taq DNA polymerase, E. coli DNA polymerase I, the Klenow fragment of E. coli DNA polymerase I, AmpliTaq DNA polymerase Stoffel fragment, T4 DNA polymerase, Hot Tub DNA polymerase, Tth DNA polymerase, Tfl DNA polymerase, Pfu or Exo-Pfu DNA Polymerase, RNA polymerase and reverse transcriptase.

21. The process of claim 1, wherein the target nucleic acid sequence contains at least one deletion or mutation that causes a genetic disease or cancer.

22. The process of claim 1, wherein the target nucleic acid sequence is contained in a plant, animal, insect, pathogenic organism, virus or oncogene.

23. The process of claim 1, wherein one of said primers comprises two or more different oligonucleotides, one of said oligonucleotides having a sequence exactly complementary to said target nucleic acid sequence.

24. The process of claim 1, wherein each of the steps is conducted sequentially without isolation or purification of the products.

25. The process of claim 24 wherein each of the steps is conducted in a single reaction medium.

26. The process of claim 1, wherein the 5' end of the first primer comprises a phosphorothioate group.

27. The process of claim 1, wherein the 3' end of the second primer comprises an arabinosyl nucleotide.

28. A process for detecting enzymatically a mutation or an allele in a target nucleic acid sequence contained in a nucleic acid or a mixture of nucleic acids, comprising the steps of:

a) selecting the target nucleic acid sequence;

b) providing primers, said primers comprising a first primer which is substantially complementary to a first segment at a first end of the target nucleic acid sequence and a second primer which is substantially complementary to a second segment at a second end of the target nucleic acid sequence and whose 3' end is adjacent to the 5' end of the first primer and a third primer which is substantially complementary to at least a portion of said first primer such that when the third primer is hybridized to the first primer, the position of the third primer complementary to the base at the 5' end of the first primer contains a modification which reduces strand displacement under polymerizing conditions, wherein one of said primers comprises two or more different oligonucleotides, one of said oligonucleotides having a sequence exactly complementary to said target nucleic acid sequence wherein each oligonucleotide is labeled with a different label;

c) providing at least four different nucleotide bases;

d) hybridizing said first and second primers to the target nucleic acid sequence in a target dependent manner to form a primer-target complex;

e) ligating under conditions such that the adjacent 5' end of the first primer and the 3' end of the second primer will ligate to form a fused amplification product substantially complementary to said target nucleic acid sequence;

f) dissociating said fused amplification product from said target nucleic acid sequence;

g) hybridizing said third primer to said fused amplification product;

h) extending said third primer in the presence of the nucleotide bases under conditions such that an extended amplification product is formed substantially complementary to said fused amplification product and which contains said modification;

i) dissociating the extended, modified amplification product from the fused amplification product;

j) allowing the extended, modified amplification product to hybridize to additional first and second primers in a target dependent manner; and k) ligating the 5' end of the additional first primer to the 3' end of the additional second primer while reducing strand displacement of the additional first primer, to form additional amplification product; and l) determining which labeled primer is contained within the fused amplification product or the extended amplification product to thereby detect whether the mutation or allele is present.

29. A process for amplifying enzymatically a target nucleic acid sequence contained in a nucleic acid or a mixture of nucleic acids comprising the steps of:

a) selecting the target nucleic acid sequence;

b) providing primers, said primers comprising a first primer which is substantially complementary to a first segment at a first end of the target nucleic acid sequence and a second primer which is substantially complementary to a second segment at a second end of the target nucleic acid sequence said second segment being spaced a number of nucleotides from said first segment, and a third primer which is substantially complementary to at least a portion of said first primer, said portion including the 5' end of the first primer such that when the third primer is hybridized to the first primer, the position of the third primer complementary to the base at the 5' end of the first primer contains a modification which reduces strand displacement under polymerizing conditions;

c) providing at least four different nucleotide bases;

d) hybridizing said first and second primers to the target nucleic acid sequence in a target dependent manner to form a primer-target complex;

e) extending the 3' end of the second primer in the presence of the nucleotide bases under conditions such that an extended second primer is formed wherein the 3' end of the extended second primer terminates at a base adjacent to the 5' end of the first primer;

f) ligating the ends of the first primer and extended second primer under conditions such that said first and said second primers will form a fused amplification product substantially complementary to said target nucleic acid sequence;

g) dissociating said fused amplification product from said target nucleic acid sequence;

h) hybridizing said third primer to said fused amplification product;

i) extending said third primer in the presence of the nucleotide bases under conditions such that an extended modified amplification product is formed substantially complementary to said fused amplification product and which contains said modification;

j) allowing the extended, modified amplification product to hybridize to additional first and second primers in a target dependent manner;

k) extending the 3' end of the additional second primer in the presence of the nucleotide bases under conditions such that an extended additional second primer is formed wherein the 3' end of the extended additional second primer terminates at a base adjacent to the 5' end of the additional first primer; and l) ligating the 5' end of the additional first primer to the 3' end of the additional second primer while reducing strand displacement of the additional first primer, to form additional amplification product.

30. The process of claim 29, wherein the modification is to the nucleotide base.

31. The process of claim 30, wherein the modification is a base selected from the group consisting of xanthine, hypoxanthine and an abasic site.

32. The process of claim 29, wherein the modification is to the nucleotide sugar moiety.

33. The process of claim 32, wherein the modification is selected from the group consisting of 2'-O-alkylribonucleotides, ribonucleotides, and arabinosyl nucleotide derivatives.

34. The process of claim 33, wherein the modification is a 2'-O-methylribonucleotide.

35. The process of claim 29, wherein the modification is to the internucleotide linkage.

36. The process of claim 35, wherein the modification is a methyl phosphonate internucleotide linkage.

37. The process of claim 29, wherein steps (d) through (j) are repeated at least once.

38. The process of claim 29, wherein the target nucleic acid is double stranded nucleic acid comprising a first and second strand wherein said first and second primers are substantially complementary to said first strand and said third primer is substantially complementary to said second strand and said first and second strands are dissociated prior to step (d), and wherein at least some of the third primers hybridize to the second strand and are extended to form an extended amplification product.

39. The process of claim 38, further comprising a fourth primer wherein the fourth primer is substantially complementary to said second target nucleic acid strand and said fourth primer is substantially complementary to said second primer, and wherein the third primer is extended to the 3' end of the fourth primer and is ligated thereto.

40. The process of claim 39, wherein the nucleic acid is denatured by heating.

41. The process of claim 29, wherein the nucleic acid is DNA from a plant, animal, insect, pathogenic organism, virus or oncogene.

42. The process of claim 29, wherein the nucleic acid is RNA.

43. The process of claim 29, wherein steps (f) and (l) are conducted in the presence of a ligating enzyme.

44. The process of claim 43, wherein the ligating enzyme is T4 DNA ligase.

45. The process of claim 43, wherein the ligating enzyme is stable at 0°–95° C.

46. The process of claim 45, wherein the ligating enzyme is selected from the group consisting of Ampligase, Taq ligase and Pfu ligase.

47. The process of claim 29 wherein steps (e), (i) and (k) are conducted in the presence of polymerase.

48. The process of claim 47, wherein the polymerase is selected from the group consisting of E. coli DNA polymerase I, Klenow fragment of E. coli DNA polymerase I and T4 DNA polymerase.

49. The process of claim 47, wherein the polymerase is stable at 0°–95° C.

50. The process of claim 49, wherein the polymerase is selected from the group consisting of Taq DNA polymerase, E. coli DNA polymerase I, the Klenow fragment of E. coli DNA polymerase I, AmpliTaq DNA polymerase Stoffel fragment, T4 DNA polymerase, Hot Tub DNA polymerase, Tth DNA polymerase, Tfl DNA polymerase, Pfu or Exo-Pfu DNA Polymerase, RNA polymerase and reverse transcriptase.

51. The process of claim 29, wherein the target nucleic acid sequence contains at least one deletion or mutation that causes a genetic disease.

52. The process of claim 29, wherein the target nucleic acid sequence is contained in a pathogenic organism, virus or oncogene.

53. The process of claim 29, wherein one of said primers comprises two or more oligonucleotides, one of said oligonucleotides having a sequence exactly complementary to said target nucleic acid.

54. The process of claim 29, wherein each of the steps is conducted sequentially without isolation or purification of the products.

55. The process of claim 54, wherein each of the steps is conducted in a single reaction medium.

56. The process of claim 29, wherein the 5' end of the first primer comprises an phosphorothioate group.

57. The process of claim 39, wherein the 5' end of the fourth primer comprises an phosphorothioate group.

58. A process for detecting enzymatically a mutation or an allele in a target nucleic acid sequence contained in a nucleic acid or a mixture of nucleic acids comprising the steps of a) selecting the target nucleic acid sequence;
b) providing primers, said primers comprising a first primer which is substantially complementary to a first segment at a first end of the target nucleic acid sequence and a second primer which is substantially complementary to a second segment at a second end of the target nucleic acid sequence said second segment being spaced from said first segment and a third primer which is substantially complementary to at least a portion of said first primer such that when the third primer is hybridized to the first primer, the position of the third primer complementary to the base at the 5' end of the first primer contains a modification which reduces strand displacement under polymerizing conditions, wherein one of said primers comprises two or more different oligonucleotides, one of said oligonucleotides having a sequence exactly complementary to said target nucleic acid sequence wherein each oligonucleotide is labeled with a different label;
c) providing at least four different nucleotide bases;
d) hybridizing said first and second primers to the target nucleic acid sequence in a target dependent manner to form a primer-target complex;
e) extending the 3' end of the second primer in the presence of the nucleotide bases under conditions such that an extended second primer is formed wherein the 3' end of the extended second primer is adjacent to the 5' end of the first primer;
f) ligating the ends of the first and second primers under conditions such that said first and said extended second primers will form a fused amplification product complementary to said target nucleic acid sequence;
g) dissociating said fused amplification product from said target nucleic acid sequence;
h) hybridizing said third primer to said fused amplification product;
i) extending said third primer in the presence of the nucleotide bases under conditions such that an extended amplification product is formed complementary to said fused amplification product and which contains said modification;
j) optionally dissociating the extended amplification product from the fused amplification product;
k) determining which labeled primer is contained within the fused amplification product or the extended amplification product to thereby detect whether the mutation or allele is present.

59. A process according to any of claims 1, 28, 29 or 58 wherein the first primer hybridizes to the target sequence prior to the second primer.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 2726 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
GATTGAGAAA  GCTGTCAAGG  AAGCCAATGC  CTATGACTTT  ATCATGAAAC  TGCCTCATAA       60
ATTTGACACC  CTGGTTGGAG  AGAGAGGGGC  CCAGTTGAGT  GGTGGGCAGA  AGCAGAGGAT      120
CGCCATTGCA  CGTGCCCTGG  TTCGCAACCC  CAAGATCCTC  CTGCTGGATG  AGGCCACGTC      180
AGCCTTGGAC  ACAGAAAGCG  AAGCAGTGGT  TCAGGTGGCT  CTGGATAAGG  CCAGAAAAGG      240
TCGGACCACC  ATTGTGATAG  CTCATCGTTT  GTCTACAGTT  CGTAATGCTG  ACGTCATCGC      300
TGGTTTCGAT  GATGGAGTCA  TTGTGGAGAA  AGGAAATCAT  GATGAACTCA  TGAAAGAGAA      360
AGGCATTTAC  TTCAAACTTG  TCACAATGCA  GACAGCAGGA  ATGAAGTTG   AATTAGAAAA      420
TGCAGCTGAT  GAATCCAAAA  GTGAAATTGA  TGCCTTGGAA  ATGTCTTCAA  ATGATTCAAG      480
ATCCAGTCTA  ATAAGAAAAA  GATCAACTCG  TAGGAGTGTC  CGTGGATCAC  AAGCCCAAGA      540
CAGAAAGCTT  AGTACCAAAG  AGGCTCTGGA  TGAAAGTATA  CCTCCAGTTT  CCTTTTGGAG      600
GATTATGAAG  CTAAATTTAA  CTGAATGGCC  TTATTTTGTT  GTTGGTGTAT  TTTGTGCCAT      660
TATAAATGGA  GGCCTGCAAC  CAGCATTTGC  AATAATATTT  TCAAAGATTA  TAGGGGTTTT      720
TACAAGAATT  GATGATCCTG  AAACAAAACG  ACAGAATAGT  AACTTGTTTT  CACTATTGTT      780
TCTAGCCCTT  GGAATTATTT  CTTTTATTAC  ATTTTTCCTT  CAGGGTTTCA  CATTTGGCAA      840
AGCTGGAGAG  ATCCTCACCA  AGCGGCTCCG  ATACATGGTT  TTCCGATCCA  TGCTCAGACA      900
GGATGTGAGT  TGGTTTGATG  ACCCTAAAAA  CACCACTGGA  GCATTGACTA  CCAGGCTCGC      960
CAATGATGCT  GCTCAAGTTA  AAGGGGCTAT  AGGTTCCAGG  CTTGCTGTAA  TTACCCAGAA     1020
TATAGCAAAT  CTTGGGACAG  GAATAATTAT  ATCCTTCATC  TATGGTTGGC  AACTAACACT     1080
GTTACTCTTA  GCAATTGTAC  CCATCATTGC  AATAGCAGGA  GTTGTTGAAA  TGAAAATGTT     1140
GTCTGGACAA  GCACTGAAAG  ATAAGAAAGA  ACTAGAAGGT  GCTGGGAAGA  TCGCTACTGA     1200
AGCAATAGAA  AACTTCCGAA  CCGTTGTTTC  TTTGACTCAG  GAGCAGAAGT  TTGAACATAT     1260
GTATGCTCAG  AGTTTGCAGG  TACCATACAG  AAACTCTTTG  AGGAAAGCAC  ACATCTTTGG     1320
AATTACATTT  TCCTTCACCC  AGGCAATGAT  GTATTTTTCC  TATGCTGGAT  GTTTCCGGTT     1380
TGGAGCCTAC  TTGGTGGCAC  ATAAACTCAT  GAGCTTTGAG  GATGTTCTGT  TAGTATTTTC     1440
```

| | | | | | |
|---|---|---|---|---|---|
| AGCTGTTGTC | TTTGGTGCCA | TGGCCGTGGG | GCAAGTCAGT | TCATTTGCTC | CTGACTATGC | 1500
| CAAAGCCAAA | ATATCAGCAG | CCCACATCAT | CATGATCATT | GAAAAACCC | CTTTGATTGA | 1560
| CAGCTACAGC | ACGGAAGGCC | TAATGCCGAA | CACATTGGAA | GGAAATGTCA | CATTTGGTGA | 1620
| AGTTGTATTC | AACTATCCCA | CCCGACCGGA | CATCCCAGTG | CTTCAGGGAC | TGAGCCTGGA | 1680
| GGTGAAGAAG | GGCCAGACGC | TGGCTCTGGT | GGGCAGCAGT | GGCTGTGGGA | AGAGCACAGT | 1740
| GGTCCAGCTC | CTGGAGCGGT | TCTACGACCC | CTTGGCAGGG | AAAGTGCTGC | TTGATGGCAA | 1800
| AGAAATAAAG | CGACTGAATG | TTCAGTGGCT | CCGAGCACAC | CTGGGCATCG | TGTCCCAGGA | 1860
| GCCCATCCTG | TTTGACTGCA | GCATTGCTGA | GAACATTGCC | TATGGAGACA | ACAGCCGGGT | 1920
| GGTGTCACAG | GAAGAGATCG | TGAGGGCAGC | AAAGGAGGCC | AACATACATG | CCTTCATCGA | 1980
| GTCACTGCCT | AATAAATATA | GCACTAAAGT | AGGAGACAAA | GGAACTCAGC | TCTCTGGTGG | 2040
| CCAGAAACAA | CGCATTGCCA | TAGCTCGTGC | CCTTGTTAGA | CAGCCTCATA | TTTTGCTTTT | 2100
| GGATGAAGCC | ACGTCAGCTC | TGGATACAGA | AAGTGAAAAG | GTTGTCCAAG | AAGCCCTGGA | 2160
| CAAAGCCAGA | GAAGGCCGCA | CCTGCATTGT | GATTGCTCAC | CGCCTGTCCA | CCATCCAGAA | 2220
| TGCAGACTTA | ATAGTGGTGT | TTCAGAATGG | CAGAGTCAAG | GAGCATGGCA | CGCATCAGCA | 2280
| GCTGCTGGCA | CAGAAAGGCA | TCTATTTTTC | AATGGTCAGT | GTCCAGGCTG | GAACAAAGCG | 2340
| CCAGTGAACT | CTGACTGTAT | GAGATGTTAA | ATACTTTTA | ATATTTGTTT | AGATATGACA | 2400
| TTTATTCAAA | GTTAAAAGCA | AACACTTACA | GAATTATGAA | GAGGTATCTG | TTTAACATTT | 2460
| CCTCAGTCAA | GTTCAGAGTC | TTCAGAGACT | TCGTAATTAA | AGGAACAGAG | TGAGAGACAT | 2520
| CATCAAGTGG | AGAGAAATCA | TAGTTTAAAC | TGCATTATAA | ATTTTATAAC | AGAATTAAAG | 2580
| TAGATTTTAA | AAGATAAAAT | GTGTAATTTT | GTTTATATTT | TCCCATTTGG | ACTGTAACTG | 2640
| ACTGCCTTGC | TAAAAGATTA | TAGAAGTAGC | AAAAAGTATT | GAAATGTTTG | CATAAAGTGT | 2700
| CTATAATAAA | ACTAAACTTT | CATGTG | | | | 2726

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

AGGTTAGTAC    CAAAGAGGCT    CTGG        24

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

ACTAACAGAA CATCCTCAAA GCTC    24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

CAACATTTTC ATTTCAACAA CTCC    24

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

TTCTTTCTTA TCTTTCAGTG CTTGTCCAGA    30

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GGAGTTGTTG AAATGAAAAT GTTGTC    26

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

GTTCGGAAGT TTTCTATTGC TTCAGTAGCG    30

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

CTACTGAAGC AATAGAAAAC TTCCGAAC         28

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

CGCCAGGGTT TTCCCAGTCA CGAC         24

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

CGTAATCATG GTCATAGCTG TTTCCTG         27

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

GGAAACAGCT ATGACCATGA TTACGA         26

( 2 ) INFORMATION FOR SEQ ID NO:12:

( i ) SEQUENCE CHARACTERISTICS:
        ( A ) LENGTH: 140 base pairs (B) TYPE: nucleic acid
(C) STRANDEDNESS: both
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

| | | | | | |
|---|---|---|---|---|---|
|CACACAGGAA|ACAGCTATGA|CCATGATTAC|GAATTCGAGC|TCGGTACCCG|GGGATCCTCT|60|
|AGAGTCGACC|TGCAGGCATG|CAAGCTTGGC|ACTGGCCGTC|GTTTTACAAC|GTCGTGACTG|120|
|GGAAAACCCT|GGCGTTACCC| | | | |140|

(2) INFORMATION FOR SEQ ID NO:13:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

CGTGACTGGG AAAACCCTGG CGTT        24

(2) INFORMATION FOR SEQ ID NO:14:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

AACATTTTCA TTTCAACAAC TCCTGC        26

(2) INFORMATION FOR SEQ ID NO:15:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: modified_base
(B) LOCATION: 28
(C) IDENTIFICATION METHOD: experimental
(D) OTHER INFORMATION: /evidence= EXPERIMENTAL
/ mod_base= OTHER
/ note= "N=ara-C"

(xi) SEQUENCE DESCRIPTION: SEQ ID NO:15:

TTTCTTATCT TTCAGTGCTT GTCCAGAN                                28

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

CCATAGGTTT TGAACTCACA G                                       21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

TGCTTCTCAG ATCCTCTGAC A                                       21

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

GTGAGTTCAA AACCTATGGG GCAT                                    24

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:19:

GGTAATCATG GTCATAGCTG TTTCCTG                                 27

( 2 ) INFORMATION FOR SEQ ID NO:20:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

```
GGAAACAGCT ATGACCATGA TTACCAATTC GAGCTCCGTC GTGACTGGGA AAACCCTGGC    60
GTT                                                                 63
```

( 2 ) INFORMATION FOR SEQ ID NO:21:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: modified_base
        ( B ) LOCATION: 25
        ( C ) IDENTIFICATION METHOD: experimental
        ( D ) OTHER INFORMATION: /evidence= EXPERIMENTAL
            / mod_base= OTHER
            / note= "N=ara-C"

( x i ) SEQUENCE DESCRIPTION: SEQ ID NO:21:

```
GGAAACAGCT ATGACCATGA TTACNAATTC GAGCTCCGTC GTGACTGGGA AAACCCTGGC    60
GTT                                                                 63
```

( 2 ) INFORMATION FOR SEQ ID NO:22:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: modified_base
        ( B ) LOCATION: 25
        ( C ) IDENTIFICATION METHOD: experimental
        ( D ) OTHER INFORMATION: /evidence= EXPERIMENTAL
            / mod_base= cm ( x i ) SEQUENCE DESCRIPTION: SEQ ID NO:22:

```
GGAAACAGCT ATGACCATGA TTACNAATTC GAGCTCCGTC GTGACTGGGA AAACCCTGGC    60
GTT                                                                 63
```

( 2 ) INFORMATION FOR SEQ ID NO:23:

( i ) SEQUENCE CHARACTERISTICS:
  ( A ) LENGTH: 63 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

GGAAACAGCT ATGACCATGA TTACCAATTC GAGCTCCGTC GTGACTGGGA AAACCCTGGC 60

GTT 63

( 2 ) INFORMATION FOR SEQ ID NO:24:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

ACGACGGAGC TCGAATT 17

( 2 ) INFORMATION FOR SEQ ID NO:25:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: modified_base
  ( B ) LOCATION: 19
  ( C ) IDENTIFICATION METHOD: experimental
  ( D ) OTHER INFORMATION: /evidence= EXPERIMENTAL
    / mod_base= OTHER
    / note= "N=ara-C"

( x i ) SEQUENCE DESCRIPTION: SEQ ID NO:25:

CCATAGGTTT TGAACTCANA G 21

( 2 ) INFORMATION FOR SEQ ID NO:26:

( i ) SEQUENCE CHARACTERISTICS:
  ( A ) LENGTH: 36 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

AAATGCCCCA TAGGTTTTGA ACTCACAGAT TAAACT 36

( 2 ) INFORMATION FOR SEQ ID NO:27:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

ACCGAGTGTC AGAGGATCTG AGAAGCAGAA TT 32